United States Patent
Sullivan et al.

(10) Patent No.: US 7,623,915 B2
(45) Date of Patent: Nov. 24, 2009

(54) INTERACTIVE FIRST AID INFORMATION SYSTEM

(75) Inventors: Joseph L. Sullivan, Kirkland, WA (US); Richard C. Nova, Kirkland, WA (US); James M. Owen, Redmond, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 1031 days.

(21) Appl. No.: 10/620,742

(22) Filed: Jul. 16, 2003

(65) Prior Publication Data

US 2005/0015115 A1    Jan. 20, 2005

(51) Int. Cl.
*A61N 1/39*     (2006.01)
*A61B 19/00*   (2006.01)
*A61H 31/00*   (2006.01)

(52) U.S. Cl. .............................. 607/5; 128/920; 705/2; 706/924; 600/300

(58) Field of Classification Search .............. 607/1–5; 600/300, 301; 128/897, 898, 903, 904, 920, 128/922–925; 601/15, 41; 705/2–3; 434/262, 434/265; 706/11, 45, 47, 924; 715/700
See application file for complete search history.

(56) References Cited

U.S. PATENT DOCUMENTS

| | | | |
|---|---|---|---|
| 3,934,226 A | 1/1976 | Stone et al. | |
| 4,118,946 A | 10/1978 | Tubin | |
| 4,290,114 A * | 9/1981 | Sinay | 600/301 |
| 4,292,973 A | 10/1981 | Yamauchi et al. | |
| 4,353,359 A | 10/1982 | Milbauer | |
| 4,610,254 A * | 9/1986 | Morgan et al. | 607/6 |
| 4,619,265 A | 10/1986 | Morgan et al. | |
| 4,638,436 A | 1/1987 | Badger et al. | |
| 4,839,822 A * | 6/1989 | Dormond et al. | 706/45 |
| 5,088,037 A * | 2/1992 | Battaglia | 600/300 |
| 5,261,243 A | 11/1993 | Dunsmore | |
| 5,285,781 A | 2/1994 | Brodard | |

(Continued)

FOREIGN PATENT DOCUMENTS

WO        WO 96/19774 A1     6/1996

(Continued)

OTHER PUBLICATIONS

Carmichael, Mary, "Medical Testing at Home," Newsweek, May 19, 2003, pp. 67-68.

(Continued)

*Primary Examiner*—Carl H Layno
*Assistant Examiner*—Jessica Reidel
(74) *Attorney, Agent, or Firm*—Shumaker & Sieffert, P.A.

(57) ABSTRACT

In general, the invention is directed to techniques for determining appropriate first aid and applying first aid that is appropriate. A first aid system receives patient status information from an input device or a sensor, and presents first aid information as a function of the received patient status information. The first aid system may be incorporated with an external defibrillator. The first aid system may acquire patient status information through an interaction with an operator, in which the first aid system asks the operator to supply patient status information. In one embodiment of the invention, the operator may supply patient status information by touching a diagram representing at least a portion of a human body.

5 Claims, 16 Drawing Sheets

U.S. PATENT DOCUMENTS

| | | | |
|---|---|---|---|
| 5,350,417 | A | 9/1994 | Augustine |
| 5,405,362 | A * | 4/1995 | Kramer et al. ............... 607/5 |
| 5,456,691 | A | 10/1995 | Snell |
| 5,474,574 | A | 12/1995 | Payne et al. |
| 5,486,204 | A | 1/1996 | Clifton |
| 5,521,812 | A | 5/1996 | Feder et al. |
| 5,571,142 | A | 11/1996 | Brown et al. |
| 5,593,426 | A * | 1/1997 | Morgan et al. ............... 607/5 |
| 5,662,690 | A | 9/1997 | Cole et al. |
| 5,724,025 | A | 3/1998 | Tavori |
| 5,836,993 | A | 11/1998 | Cole |
| 5,850,630 | A | 12/1998 | Wilson |
| 5,913,685 | A * | 6/1999 | Hutchins ............... 434/265 |
| 6,012,179 | A | 1/2000 | Garrett et al. |
| 6,091,989 | A | 7/2000 | Swerdlow et al. |
| 6,101,413 | A | 8/2000 | Olson et al. |
| 6,141,584 | A | 10/2000 | Rockwell et al. |
| 6,148,233 | A | 11/2000 | Owen et al. |
| 6,201,992 | B1 * | 3/2001 | Freeman ............... 607/5 |
| 6,209,144 | B1 | 4/2001 | Carter |
| 6,269,267 | B1 | 7/2001 | Bardy et al. |
| 6,277,143 | B1 | 8/2001 | Klatz et al. |
| 6,301,502 | B1 | 10/2001 | Owen et al. |
| 6,321,113 | B1 | 11/2001 | Parker et al. |
| 6,334,070 | B1 | 12/2001 | Nova et al. |
| 6,356,785 | B1 | 3/2002 | Snyder et al. |
| 6,370,428 | B1 | 4/2002 | Snyder et al. |
| 6,383,135 | B1 * | 5/2002 | Chikovani et al. ............ 600/300 |
| 6,389,828 | B1 | 5/2002 | Thomas |
| 6,406,427 | B1 | 6/2002 | Williams et al. |
| 6,409,745 | B1 | 6/2002 | Ducharme et al. |
| 6,416,480 | B1 | 7/2002 | Nenov |
| 6,426,759 | B1 | 7/2002 | Ting et al. |
| 6,461,379 | B1 | 10/2002 | Carson et al. |
| 6,468,210 | B1 | 10/2002 | Iliff |
| 6,473,920 | B2 | 11/2002 | Augustine et al. |
| 6,475,143 | B2 | 11/2002 | Iliff |
| 6,497,358 | B1 | 12/2002 | Walsh |
| 6,524,241 | B2 | 2/2003 | Iliff |
| 6,527,713 | B2 | 3/2003 | Iliff |
| 6,569,093 | B2 | 5/2003 | Iliff |
| 6,581,400 | B2 | 6/2003 | Augustine et al. |
| 6,682,550 | B2 | 1/2004 | Clifton et al. |
| 6,697,671 | B1 | 2/2004 | Nova et al. |
| 6,813,517 | B2 | 11/2004 | Daynes et al. |
| 6,829,501 | B2 | 12/2004 | Nielsen et al. |
| 6,887,199 | B2 | 5/2005 | Bridger et al. |
| 2001/0047140 | A1 * | 11/2001 | Freeman ............... 601/41 |
| 2001/0049545 | A1 | 12/2001 | Lasersohn et al. |
| 2002/0004729 | A1 | 1/2002 | Zak et al. |
| 2002/0072785 | A1 | 6/2002 | Nelson et al. |
| 2002/0103508 | A1 | 8/2002 | Mathur |
| 2002/0138302 | A1 | 9/2002 | Bodnick |
| 2002/0143366 | A1 | 10/2002 | Herleikson |
| 2003/0023461 | A1 | 1/2003 | Quintanilla et al. |
| 2003/0088284 | A1 | 5/2003 | Daynes et al. |
| 2003/0146942 | A1 * | 8/2003 | Helgason et al. ............ 345/968 |
| 2003/0195567 | A1 | 10/2003 | Jayne et al. |
| 2004/0064342 | A1 * | 4/2004 | Browne et al. ............... 705/2 |
| 2004/0078215 | A1 * | 4/2004 | Dahlin et al. ............... 705/2 |
| 2004/0136578 | A1 * | 7/2004 | Sieracki et al. ............ 382/128 |
| 2004/0249419 | A1 * | 12/2004 | Chapman et al. ............ 607/5 |

FOREIGN PATENT DOCUMENTS

| | | |
|---|---|---|
| WO | WO 99/44552 A1 | 9/1999 |
| WO | WO 00/33236 A1 | 6/2000 |
| WO | WO 01/85566 A1 | 11/2001 |
| WO | WO 01/95977 A1 | 12/2001 |
| WO | WO 02/41231 A2 | 5/2002 |
| WO | WO 03/003912 A1 | 1/2003 |

OTHER PUBLICATIONS

U.S. Appl. No. 10/810,045, filed Mar. 26, 2004, titled "Defibrillators Customized for Anticipated Patients."

The International Search Report and The Written Opinion of the International Searching Authority for International Application No. PCT/US2004/022349 mailed Dec. 15, 2004 (7 pages).

Sophie Cluet and Claude Delobel, "A General Framework for the Optimization of Object-Oriented Queries," ACM SIGMOD Record vol. 21, Issue 2, pp. 383-392 (Jun. 1992).

Medusa Medical Technologies, Inc. home page, archive dated May 5, 2002, downloaded from http://web.archive.org/web/20020808172506/www.medusa.ca/aboutus.htm on Mar. 26, 2006 (2 pages).

Medusa Medical Technologies, Inc. SIREN product page, archive dated May 5, 2002, downloaded from http://web.archive.org/web/20020905071213/www.medusa.ca/products.htm on Mar. 26, 2006 (4 pages).

HealthWare Solutions home page, archive dated Sep. 27, 2002, downloaded from "Internet Archive Way Back Machine," web.archive.org, on Mar. 26, 2006 (1 page).

HealthWare Solutions, "EMS Software that Works as Hard as You Do," archive dated Sep. 27, 2002, downloaded from "Internet Archive Way Back Machine," web.archive.org, on Mar. 26, 2006 (1 page).

HealthWare Solutions, "EMS Solution 2000 Administrator, Manager, Query and Desktop Manager," archive dated Sep. 27, 2002, downloaded from "Internet Archive Way Back Machine," web.archive.org, on Mar. 26, 2006 (1 page).

HealthWare Solutions, "EMS Solution 2000 Notes," archive dated Sep. 27, 2002, downloaded from "Internet Archive Way Back Machine," web.archive.org, on Mar. 26, 2006 (1 page).

HealthWare Solutions, "EMS Solution 2000 LifePak Module, NFIRS Interface, Billing Interfaces and State Interfaces," archive dated Sep. 27, 2002, downloaded from "Internet Archive Way Back Machine," web.archive.org, on Mar. 26, 2006 (1 page).

HealthWare Solutions, "EMS Solution 2000 New Products," archive dated Sep. 27, 2002, downloaded from "Internet Archive Way Back Machine," web.archive.org, on Mar. 26, 2006 (1 page).

International Preliminary Report on Patentability from corresponding PCT Application Serial No. PCT/US2004/022349 mailed on Jan. 26, 2006 (6 pages).

* cited by examiner

INTERACTIVE FIRST AID INFORMATION SYSTEM

TECHNICAL FIELD

The invention relates to medical devices, and more particularly, to medical devices used in the application of first aid.

BACKGROUND

When a patient experiences a medical emergency, it may be important for the patient to begin receiving medical care as soon as possible. In some cases, the first persons to administer medical care or assistance are persons other than trained medical personnel. This immediate medical assistance or emergency care, usually rendered by a person or persons other than trained medical personnel, is called "first aid."

First aid can greatly affect the outcome of a medical emergency. In some cases, the medical emergency can be resolved by the application of first aid alone. In other cases, first aid provides valuable assistance to the patient until trained medical personnel can treat the patient.

Some venues such as restaurants, sporting facilities, shopping malls and auditoriums have first aid kits on site. Inside a typical first aid kit is an assortment of supplies that can be used by a person to aid in providing medical care. The first aid kit can also include instructions, such as a first aid manual, which provides instruction to the untrained person about how to provide medical care. The first aid instructions typically employ common language and non-technical terms for the benefit of a person not trained to provide medical care.

Some venues also have on site medical devices applicable to specific medical situations. One such device is an automated external defibrillators (AED). In general, an AED is a device that can detect fibrillation in the heart of a patient and deliver defibrillation therapy to terminate the fibrillation and restore a sinus rhythm.

SUMMARY

In general, the invention is directed to techniques for determining appropriate first aid and applying first aid that is appropriate. A first aid system collects and processes patient status information, e.g., information pertaining to the condition, status, appearance, age, gender, weight, vital signs, symptoms or complaints of a patient. Although a patient may use the first aid system by himself, the invention will be described in the context of use by at least one operator, who interacts with the first aid system and who administers the first aid.

The first aid system may receive the patient status information from the operator or from one or more sensors. The first aid system presents first aid information as a function of the received patient status information.

"First aid information" is any data pertaining to first aid. One example of first aid information is a presumptive first aid diagnosis, which is an identification of the nature or cause of the condition of the patient, based upon the received patient status information. First aid information also includes first aid instructions, such as directions concerning the use of a first aid supply or directions pertaining to an application of a first aid technique. In general, first aid instructions are associated with particular presumptive first aid diagnoses, and the first aid system presents first aid information according to the presumptive diagnosis that seems to best describe the actual condition of the patient.

The first aid system may acquire patient status information through iterative interaction with the operator. The first aid system may, for example, interrogate the operator about a general condition of the patient, and may receive patient status information from the operator in response to the interrogation. The first aid system may then direct a more specific interrogation to the operator as a function of the received patient status information.

The interaction may be by presentation of a menu, or by a series of yes-no questions, or by other interrogation techniques. In one embodiment, the invention is directed to a method that includes displaying a diagram representing at least a portion of a human body and receiving a selection of a part of the displayed human body. The method further includes presenting first aid information as a function of the selection. This method may be useful in emergencies in which the patient reports severe pain. By pointing to a diagram, the operator can enter patient status information, i.e., the location where the patient is experiencing pain.

In another embodiment, the invention is directed to a method comprising presenting a menu of patient conditions, receiving a selection from the menu, and presenting first aid information as a function of the selection. The method can further comprise receiving additional patient status information from an input device or a sensor, or both, and presenting the first aid information as a function of the patient status information. Also in some applications, the method further comprises generating an interrogation as a function of the selection, receiving a response to the interrogation and presenting the first aid information as a function of the response.

In further embodiments, the invention is directed to a device comprising an electrical source to generate electrotherapy, such as a defibrillation shock, at least two electrodes coupled to the electrical source to deliver the electrotherapy to a patient, and at least one output device to communicate first aid information to a person. The device can further comprise one or more input devices and sensors to receive patient status information. The device can also include a compartment to hold a first aid supply.

In an additional embodiment, the invention presents a method comprising receiving a first aid procedure, storing the first aid procedure in memory and presenting first aid information as a function of the first aid procedure.

In another embodiment, the invention is directed to a method comprising requesting first patient status information, receiving the first patient status information, storing the received first patient status information in memory, receiving second patient status information, and presenting first aid information as a function of the first and second patient status information. Examples of the first patient status information include information about the patient, such as age, birth date, gender, ethnicity, height, weight, medical history, and a medication taken by the patient.

In a further embodiment, the invention is directed to a method comprising directing a person to apply at least one defibrillation electrode to a conscious patient. The method further includes measuring the electrocardiogram of the patient via the defibrillation electrode and presenting first aid information as a function of the measurement.

In an added embodiment, the invention is directed to a system comprising a first sensor to receive first patient status information, a second sensor to receive second patient status information, and at least one output device to present first aid information.

In another embodiment, the invention is directed to a method comprising receiving an identification of a patient, retrieving from memory patient status information associated with the identified patient, and presenting first aid information as a function of the patient status information. The identification of the patient may be made with the assistance of the operator or with the assistance of a sensor, such as a fingerprint sensor or eye scanner.

The invention further includes computer-readable media comprising instructions for causing a programmable processor to carry out the methods described above.

The details of one or more embodiments of the invention are set forth in the accompanying drawings and the description below. Other features and objects of the invention will be apparent from the description and drawings, and from the claims.

DETAILED DESCRIPTION

Figure 1:
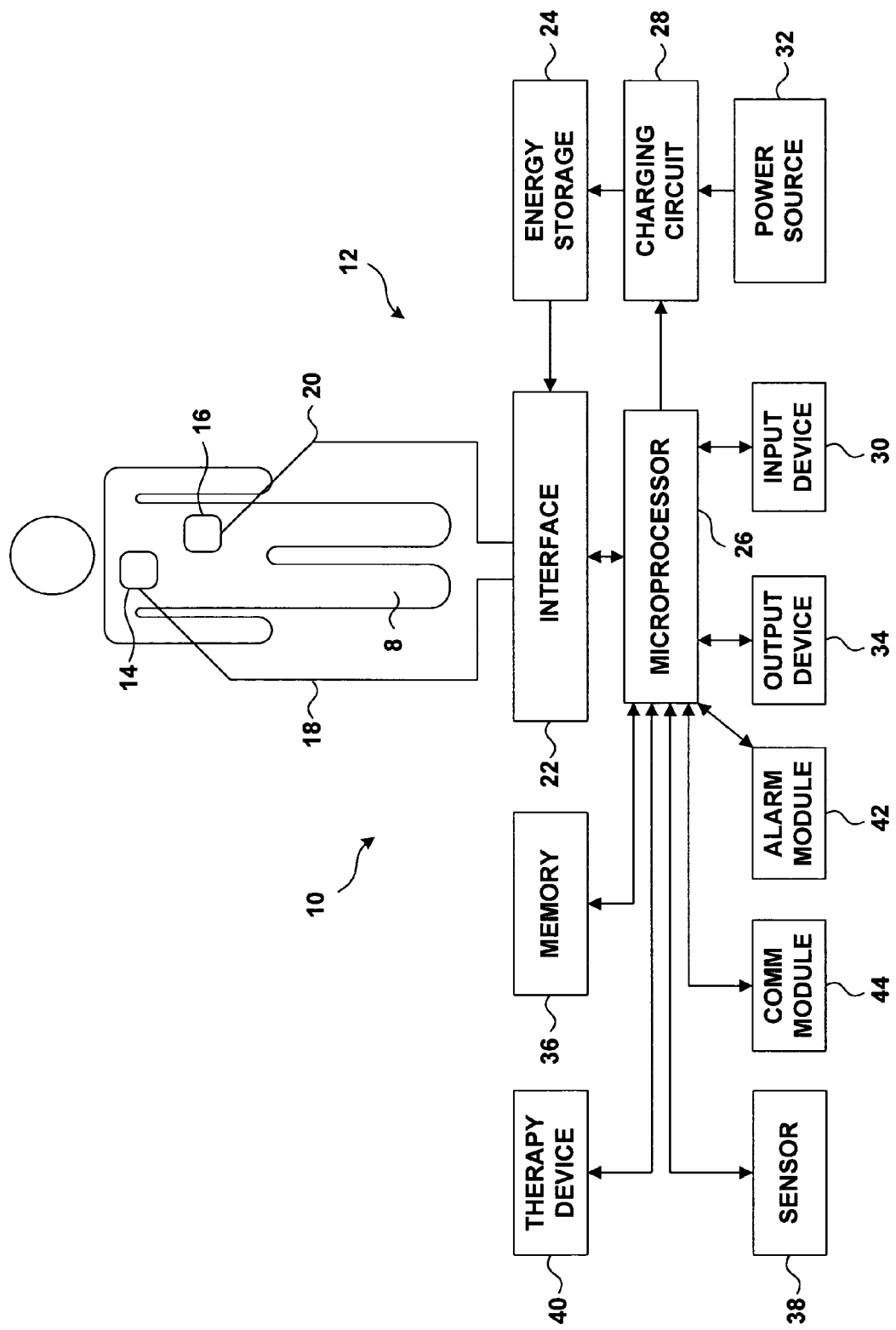
FIG. 1 is a block diagram of a first aid system incorporated with a defibrillator that may practice the techniques of the invention.

FIG. 1 is a block diagram showing a patient 8 with an exemplary first aid system 10. In FIG. 1, first aid system 10 is incorporated with an external defibrillator 12. As a result of the incorporation, certain components used for administering an electrotherapy, such as defibrillation therapy, may also be used and for general first aid administration. Defibrillator 12 is an example of a medical device with which the invention may be practiced, but the invention is not limited to practice with a defibrillator. The invention may be practiced with other medical devices that monitor or administer therapy to patient 8, such as an electronic blood pressure monitor. The invention may also be practiced as a "stand-alone" application, i.e., a first aid system not associated with a medical device that monitors or administers therapy to patient 8.

An operator administers first aid to patient 8 with the assistance of first aid system 10. In some circumstances, the patient and the operator may be the same person, i.e., the patient may use first aid system 10 to administer first aid to himself. For simplicity, however, it will be assumed that the operator and the patient are distinct persons. The operator is assumed to have limited training in medical care.

In addition to conventional first aid, the operator may also administer an electrotherapy to patient 8 with defibrillator 12, which may be an automated external defibrillator (AED). Electrotherapy includes any of a several therapies that administer electrical stimulations to patient 8., such as pacing therapy and defibrillation therapy. For simplicity, defibrillation therapy will be described as an exemplary form of electrotherapy.

Defibrillator 12 administers defibrillation therapy to patient 8 via electrodes 14 and 16, which can be hand-held electrode paddles or adhesive electrode pads placed on the skin of patient 8. The body of patient 8 provides an electrical path between electrodes 14 and 16.

Electrodes 14 and 16 are coupled to defibrillator 12 via conductors 18 and 20 and interface 22. In a typical application, interface 22 includes a receptacle, and connectors 18, 20 plug into the receptacle. Electrical impulses or signals are sensed by defibrillator 12 via electrodes 14 and 16 and interface 22. Electrical impulses or signals are also delivered from defibrillator 12 to patient 8 via electrodes 14 and 16 and interface 22.

Interface 22 includes a switch (not shown in FIG. 1) that, when activated, couples an energy storage device 24 to electrodes 14 and 16. Energy storage device 24 stores the energy for a dosage of energy or current to be delivered to patient 8. The switch can be of conventional design and can be formed, for example, of electrically operated relays. Alternatively, the switch can comprise an arrangement of solid-state devices such as silicon-controlled rectifiers or insulated gate bipolar transistors.

Energy storage device 24 includes components, such as one or more capacitors, that store the energy to be delivered to patient 8 via electrodes 14 and 16. Before a defibrillation shock may be delivered to patient 8, energy storage device 24 is charged. A microprocessor 26 directs a charging circuit 28 to charge energy storage device 24 to a high voltage level. Charging circuit 28 comprises, for example, a flyback charger that transfers energy from a power source 32 to energy storage device 24. Power source 32 may comprise, for example, batteries and/or an adapter to an exterior power source such as an electrical outlet. In addition to supplying energy to charging circuit 28 and energy storage device 24, power source 32 also supplies power to other components of external defibrillator 12 via a power supply circuit (not shown in FIG. 1).

When microprocessor 26 determines, based upon electrical signals sensed via electrodes 14 and 16, that a defibrillation shock is indicated, microprocessor 26 automatically directs charging circuit 28 to begin charging. When the energy stored in energy storage device 24 reaches the desired level, defibrillator 12 is ready to deliver the defibrillation shock. Defibrillator 12 delivers the shock either automatically or manually.

Defibrillator 12 interacts with the operator via one or more input devices 30 and one or more output devices 34. Input device 30 may comprise, for example, one or more buttons, a keyboard, a touch screen, a voice recognition module or a pointing tool. Output device 34 may include a touch screen, a liquid crystal display (LCD display), a light emitting diode (LED) display, an organic LED (OLED) display, a cathode ray tube (CRT) display, an electroluminescent display, a plasma display, an audible sound generator, a synthetic speech module, a printer or an indicator light.

Defibrillator 12 notifies the operator that charging is completed using output device 34. The operator can acknowledge the notification and can indicate readiness using input device 30. In some embodiments, the operator triggers delivery of a defibrillation shock by pressing a button. Defibrillator 12 delivers a defibrillation shock to patient 8.

Microprocessor 26 controls delivery of defibrillation therapy. In addition to controlling the delivery of a defibrillation shock, microprocessor 26 modulates the electrical shock delivered to patient 8. Microprocessor 26 can, for example, regulate the shape of the waveform of one or more electrical pulses and the duration of the pulses. Microprocessor 26 also monitors electrocardiogram (ECG) signals sensed via electrodes 14 and 16, and may determine whether a defibrillation shock is indicated as a function the ECG signals. Microprocessor 26 can also evaluate the efficacy of administered defibrillation therapy.

In addition, microprocessor 26 controls delivery of therapy via one or more other therapy devices 40. Therapy device 40 may be any device that administers therapy to patient 8. One example of therapy device 40 is an automated chest thumper, which can mechanically administer chest compressions to patient 8. Some embodiments of the invention do not include any therapy device 40, and rely on the operator to administer therapy.

Further, as described in more detail below, microprocessor 26 controls collection and organization of information pertaining to administration of first aid. In particular, microprocessor 26 processes information to determine one or more presumptive first aid diagnoses. Microprocessor 26 controls interrogation of the operator via input device 30 and output device 34 concerning the condition of patient 8. Microprocessor 26 further analyses other data such as the ECG signals sensed via electrodes 14 and 16. Microprocessor 26 also receives input from one or more sensors 38. Microprocessor 26 uses patient status information received via electrodes 14, 16, input device 30, and sensors 38 to determine a presumptive first aid diagnosis and to present other first aid information.

Sensor 38 measures or detects patient status information, such as the vital signs of patient 8 or any other symptom or condition. Sensor 38 can include, for example, a temperature sensor, an ECG monitor such as a Holter monitor, an oxygen sensor, a carbon dioxide sensor, a respiratory sensor, and a blood pressure monitor. Sensor 38 can also include an expanded electrode set, such as a twelve-, five- or three-lead electrode set. An expanded electrode set can be used to detect ECG signals more efficiently than electrodes 14 and 16, and can be used to provide a more thorough analysis of a condition of the heart of patient 8. Microprocessor 26 analyzes data from sensor 38 and may store the data in memory 36.

Sensor 38 also includes devices that can identify patient 8, such as a voice recognition module, a fingerprint scanner or a retinal scanner. In some cases, first aid system may be customized for one or more specific patients, and identification of a particular patient causes previously stored patient status information for that patient to be retrieved. First aid system 10 can also learn the identity of patient 8 in other ways, as will be described below.

Memory 36 can include volatile storage, such as random access memory, and/or non-volatile storage, such as Flash memory or a hard disk. Memory 36 stores instructions that direct the operation of microprocessor 26. In addition, memory 36 stores data concerning patient 8 and defibrillator 12, as well as events, such as an administered defibrillation therapy or readings from sensors 38.

Memory 36 also stores "first aid information," which is any data pertaining to first aid. First aid information includes a "presumptive first aid diagnosis," which is an identification of the nature or cause of the condition of patient 8, based upon patient status information received via electrodes 14, 16, input device 30, and sensors 38. A presumptive first aid diagnosis may be general or specific.

First aid information also includes "first aid instructions," which are any instructions that pertain to rendering of first aid. First aid instructions include directions to the operator about using apparatus such as sensor 38 or a therapy device 40. First aid instructions also include directions to the operator concerning the use of a first aid supply, such as directions for application of a bandage. First aid instructions further include directions to the operator pertaining to an application of a first aid technique, such as techniques to stop bleeding.

First aid information also includes "first aid procedures," which relate first aid instructions and presumptive first aid diagnoses, and which are used by microprocessor 26 to determine a presumptive first aid diagnosis. A first aid procedure is a general plan by which first aid system 10 can determine a presumptive first aid diagnosis and present first aid information as a function of patient status information. By applying a first aid procedure, first aid system 10 narrows down the number of possible presumptive first aid diagnoses, and focuses on first aid for the particular problem experienced by patient 8. A single condition or symptom, such as feeling faint, may be associated with several possible specific presumptive diagnoses, such as low blood pressure, low blood sugar, heat exhaustion, stress or stroke. By interaction with the operator via input and output devices 30, 34, and by analyzing patient status information received via electrodes 14, 16 and sensors 38, microprocessor 26 focuses upon a presumptive first aid diagnosis. Examples of first aid procedures and techniques for focusing upon a presumptive first aid diagnosis will be discussed below.

Typically each presumptive first aid diagnosis is associated with first aid information appropriate to that presumptive diagnosis. When the presumptive first aid diagnosis is an abrasion, for example, first aid system 10 may present the operator with first aid information pertaining to treatment of an abrasion. A general presumptive first aid diagnosis, such as a presumptive diagnosis that the patient feels faint, may be associated with general first aid information, such as a direction that the patient should be instructed to lie down. A more specific presumptive first aid diagnosis, such as a presumptive diagnosis that the patient is going into shock, may be associated with more specific first aid information, such as a direction that the patient should be kept warm and comfortable and that fluids should not be administered.

First aid information generally employs a level of language that can be understood by someone not trained to provide medical care. First aid information is not limited to written or verbal information, however, but further includes graphical information as well. For example, a first aid graphic can include a diagram of a human body with associated text asking for the operator to indicate the site on the body where the patient feels pain. Graphical first aid information can be presented as any combination of animation, video clip, stepwise instructions, flow diagram, picture, drawing or the like. First aid information further includes audible alarms or alerts that call the attention of the operator to a matter of importance.

First aid system 10 interacts with the operator through input device 30 and output device 34. The interactions can occur in a number of ways. In an exemplary interaction, first aid system 10 presents a menu of patient conditions via output device 34. First aid system 10 may, for example, present the menu by displaying the menu on a touch screen. The operator uses input device 30, which may include the same touch screen, to select the patient condition from the menu that most closely describes the circumstances of patient 8. Microprocessor 26 presents first aid information to the operator as a function of the selected patient condition.

Selection of a patient condition from a menu is one way in which first aid system 10 receives "patient status information," which includes any information pertaining to the condition, status, appearance, age, gender, weight, vital signs, symptoms or complaints of patient 8. As will be described in detail below, there are many other techniques by which first aid system 10 can acquire patient status information.

Furthermore, as described in more detail below, first aid system 10 and the operator can interact iteratively. For example, output device 34 may present a menu of general conditions that relate to frequently encountered medical situations, such as "unconscious" or "severe pain." After the operator makes a selection from the menu and first aid system 10 receives the selection, first aid system 10 may display a second menu comprising more specific patient conditions.

With each interaction, first aid system 10 focuses on a possible presumptive diagnosis. A response by the operator to one interrogation may cause first aid system 10 to generate a second, more specific interrogation that can lead to determination of a presumptive diagnosis. By receiving more specific information about the patient condition, first aid system 10 focuses in on the nature of the condition of the patient by considering presumptive diagnoses that are more likely, and by eliminating presumptive diagnoses that are less likely. In some circumstances, first aid system 10 may determine a general presumptive diagnosis, then interact with the operator to determine a more specific presumptive diagnosis.

Interaction between the operator and first aid system 10 may be include a series of menu-driven interrogations and responses. The interaction need not be menu-driven, however, and other interaction techniques are described below. Furthermore, the interaction may include instructions that direct the operator to apply one or more sensors 38 to patient 8. First aid system 10 can use data collected via one or more sensors 38 to focus on a possible presumptive diagnosis.

In some circumstances, iterative interaction is unnecessary. In particular, the operator may be aware of patient status information without progressing through the iterative presentation of first aid information and associated entry of patient conditions. Instead, first aid system 10 can give the operator the option to enter patient status information directly, e.g., by entering a specific symptom or by selecting a condition from an alphabetized index.

First aid system 10 may present first aid information as a function of patient status information other than or in addition to patient status information received from the operator. For example, first aid system 10 may present first aid information as a function of ECG data received via sensors 38 or electrodes 14 and 16. First aid system 10 may direct the operator may couple electrodes 14 and 16 to patient 8 when patient 8 exhibits chest pains, is unconsciousness, or presents other signs of a heart problem. As will be described below, first aid system 10 may also direct the operator to couple electrodes 14 and 16 to patient 8 under circumstances that ordinarily may not require defibrillation therapy.

First aid system 10 may present first aid information in the form of a presumptive first aid diagnosis. In general, a "presumptive first aid diagnosis" is a probable identification of the condition of patient 8 or the cause of the condition, based upon patient status information received via electrodes 14 and 16, input device 30 or sensor 38 or any combination thereof. The diagnosis is "presumptive" in the sense that it presumes that the received patient status information is correct.

In place of or in addition to a presumptive first aid diagnosis, first aid system 10 may present first aid information in the form of instructions for further treatment of patient 8, or further information concerning the condition of patient 8. First aid system 10 may, for example, tell the operator which first aid supply to use and how to use it, or instruct the operator as to an application of a first aid technique, such as an instruction to elevate the legs of patient 8. First aid system 10 may also direct the operator to apply therapy device 40 and may instruct the operator in the application of therapy device 40.

Some circumstances may call for the prompt attention of the operator, and first aid system 10 may generate first aid information in the form of an alarm or an alert to direct the attention of the operator to the matter needing attention. First aid system 10 may generate an audible or visible alarm or alert with alarm module 42. Alarm module 42 can notify the operator of a critical patient condition, or of a need to supply important patient status information, or the occurrence of a pending defibrillation shock, or the like.

First aid system 10 may further include a communication module 44. Communication module 44 may be configured to summon emergency medical personnel. Communication module 44 can include a wireless communication device, such as a cellular phone, that calls an emergency service to summon emergency medical personnel. Communication module 44 may further be configured to establish a communications link with a network, as described below.

Figure 2:
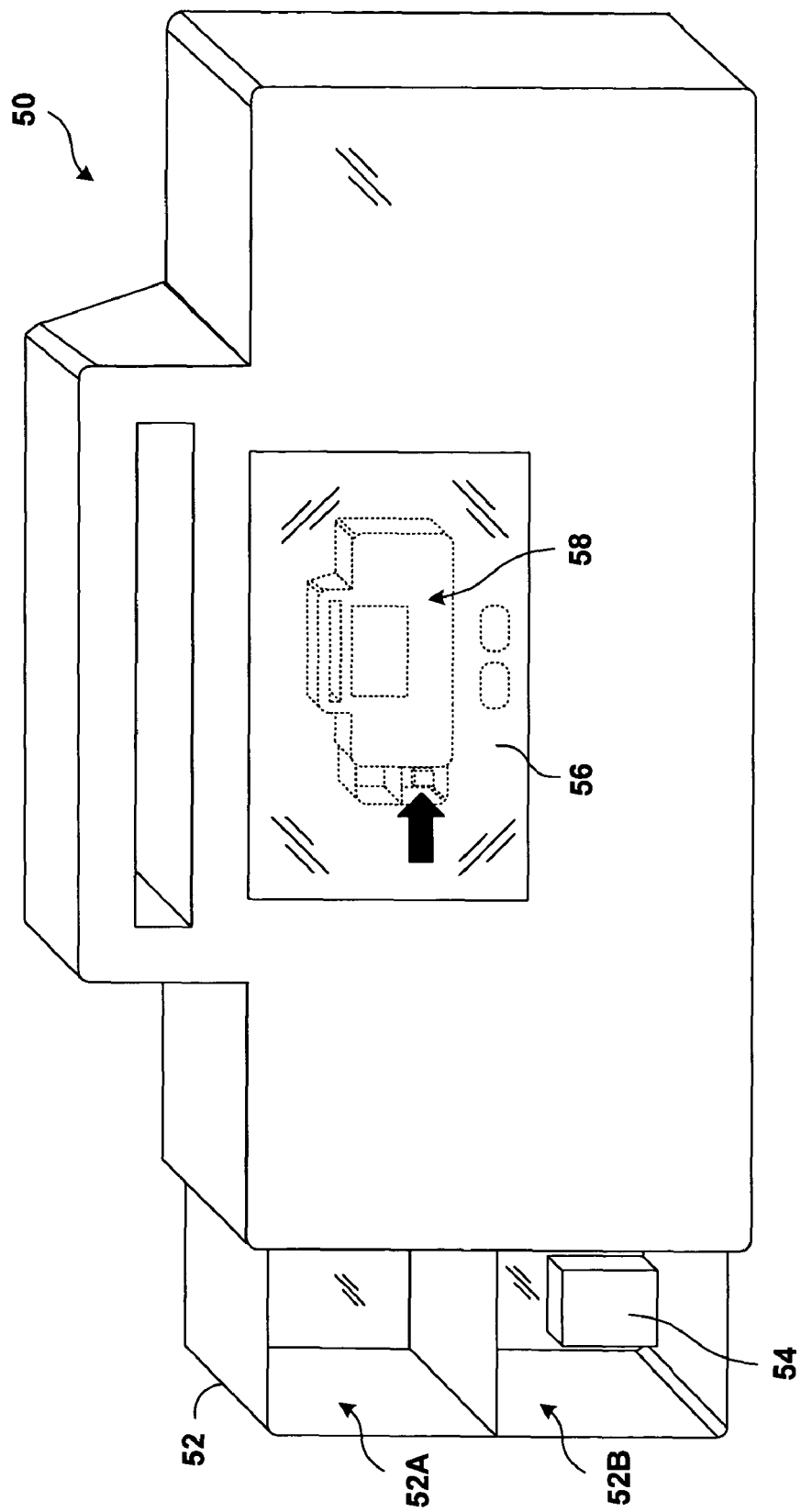
FIG. 2 is a diagram illustrating an example of a housing for a defibrillator with a first aid supply compartment, in accordance with the invention.

FIG. 2 is a diagram illustrating a housing 50 that serves as a carrying case for a first aid system. As depicted in FIG. 2, housing 50 is a carrying case for an external defibrillator such as defibrillator 12. Housing 50 includes a first aid supply compartment 52, which holds first aid supplies 54. Typical first aid supplies 54 can include bandages, gauze, scissors, medication and the like. In the embodiment shown in FIG. 2, first aid supply compartment 52 is implemented as a drawer built into housing 50, and is divided into smaller compartments 52A, 52B, to aid in organization and labeling of first aid supplies. First aid supply compartment 52 need not be implemented as a drawer, but may be implemented in other configurations, such as a cabinet built into housing 50 or a pouch coupled to housing 50.

Housing 50 includes at least one input device and output device to interact with the operator. As depicted in FIG. 2, housing 50 includes touch screen display 56. Display 56 can present interrogations concerning the condition of the patient and can present first aid information to the operator. As shown in FIG. 2, the first aid information can include a graphical illustration 58 to show the operator where a particular first aid supply is stored. Display 56 can further instruct the operator concerning use of the first aid supply 54.

There are many variations on the embodiment depicted in FIG. 2. For example, housing 50 may include open like a suitcase, allowing access to electrodes 14 and 16, and display 56 may be deployed in the interior of housing 50. Although housing 50 need not include a touch screen display, the invention will be described in terms of information presented by a display such as touch screen.

As already mentioned, first aid system 10 may be incorporated with medical devices other than a defibrillator. Accordingly, housing 50 may comprise a carrying case for other medical devices, such as an electronic blood pressure cuff or an electronic thermometer. In some embodiments of the invention, the first aid system includes no associated monitoring or therapy devices, and in these embodiments, housing 50 serves as a carrying case for first aid supplies 54.

Figure 3:
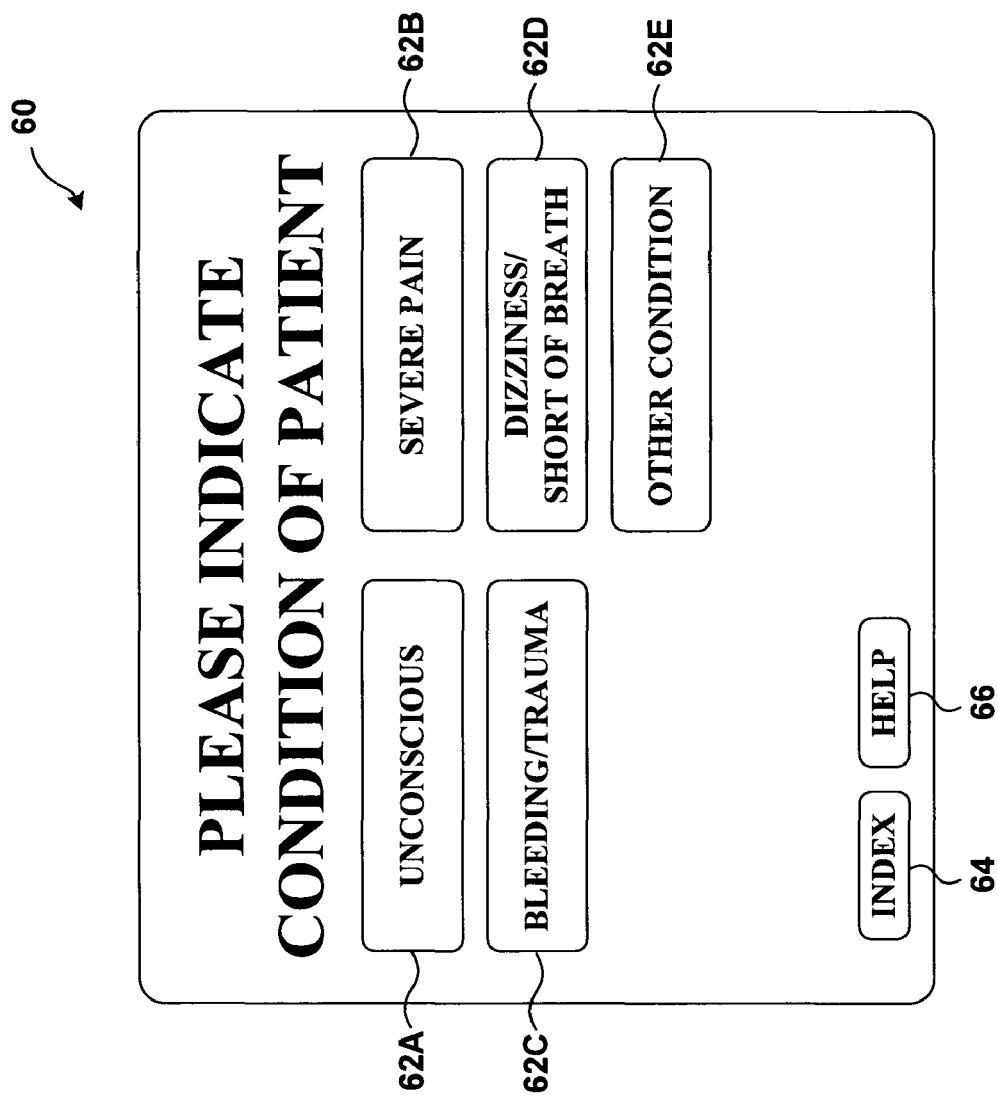
FIG. 3 is an exemplary screen display illustrating the presentation of first aid information in the form of a menu of conditions, according to one embodiment of the invention.

FIG. 3 is an exemplary screen display 60 that may be used in a first aid system and that may be presented on an output device system such as a touch screen display. Screen display 60 illustrates the presentation of first aid information, and in particular, a menu of patient conditions 62A-62E (collectively 62).

The menu of screen display 60 may be a default introductory screen presented to the operator when the operator initially activates the first aid system. Screen display 60 may be appropriate when the first aid system is deployed in a public location. In some cases, however, the first aid system may be principally for the benefit of specific individuals, such as the members of a family residing in a household. In that embodiment, the introductory screen may be replaced by a request that the patient may be identified. The introductory screen may present a list of potential patients, along with the names of the family members. A technique for receiving and storing patient status information for one or more potential patients will be described below. An "Another Person" option may also be presented, in the event the patient is not a member of the family or a person for which any patient status information has been previously stored.

When the introductory screen presents a list of possible patients, selection of a patient efficiently inputs one or more items of patient status information that have been previously stored in the first aid system. For example, the gender of the patient may be established. The age, weight, and ethnicity of the patient may also be established, along with the medical history of the patient. Each of these items of patient status information may be important in determining a presumptive first aid diagnosis, and may be important in reaching the presumptive diagnosis more quickly. If the medical history of a patient includes a previous heart attack, a past trauma, a history of taking a particular medication, a history of high blood pressure, or any other medical event, the first aid system may use this information to determine the presumptive diagnosis. In addition, use of the first aid system may automatically update the medical history of the particular patient for future use. Following identification of the patient, the first aid system may present screen display 60.

Listed conditions 62 may represent the most common conditions that the operator is likely to encounter, or the most serious conditions. As depicted in FIG. 3, menu 62 lists serious conditions first: unconsciousness, bleeding or trauma, severe pain, and dizziness or shortness of breath. Listed conditions 62 are for purposes of illustration, and more, fewer, or different conditions may be displayed. One of the selections, shown as "Other Condition," may be selected when the patient's condition is not on the menu. The operator can select any of conditions with an input device, e.g., by touching the screen at the appropriate place.

The operator may also be given an option of selecting an index 64. When the operator selects index 64, the screen displays an index of medical conditions or diagnoses, and the operator may select a topic from the index. The operator may select "Heartburn," for example, the first aid system may present first aid information about heartburn without an iterative interaction between the first aid system and the operator. The "Index" feature may further allow the operator to use the first aid system as a reference, and obtain a presentation of first aid information about a variety of subjects. In other illustrative screen displays described below, the "Index" option may be available.

The operator may also be given the option of requesting help 66. Like the "Index" option, the "Help" option may be available on several screen displays. Although the "Help" option may refresh the recollection of the operator concerning operation of the first aid system, an advantage of the menu-driven and other interactive techniques described herein is that the techniques are logical and intuitive. In an emergency, the operator may successfully use the first aid system without having his recollection fully refreshed.

When the operator selects a condition 62 from the menu, the menu may disappear from the display and different information may appear on the display, according the selection. In particular, the microprocessor retrieves information stored in memory as a function of patient status information indicated by the selection and displays the information. The displayed information may comprise first aid information, which may include a presumptive first aid diagnosis, instructions for using a first aid supply, or directions for applying a first aid technique in word or graphical form. The displayed information may further include interrogations that ask the operator to provide additional patient status information.

Should the operator select "Bleeding/Trauma," for example, the first aid system may interrogate the operator about the site of bleeding or the nature of the trauma. Should the operator select "Severe Pain," the first aid system may interrogate the operator about the location, nature and extent of the pain. Further interrogation may be by a menu, similar to that depicted in FIG. 3, or by a series of "yes-no" questions, or by other interrogation techniques.

Figure 4:
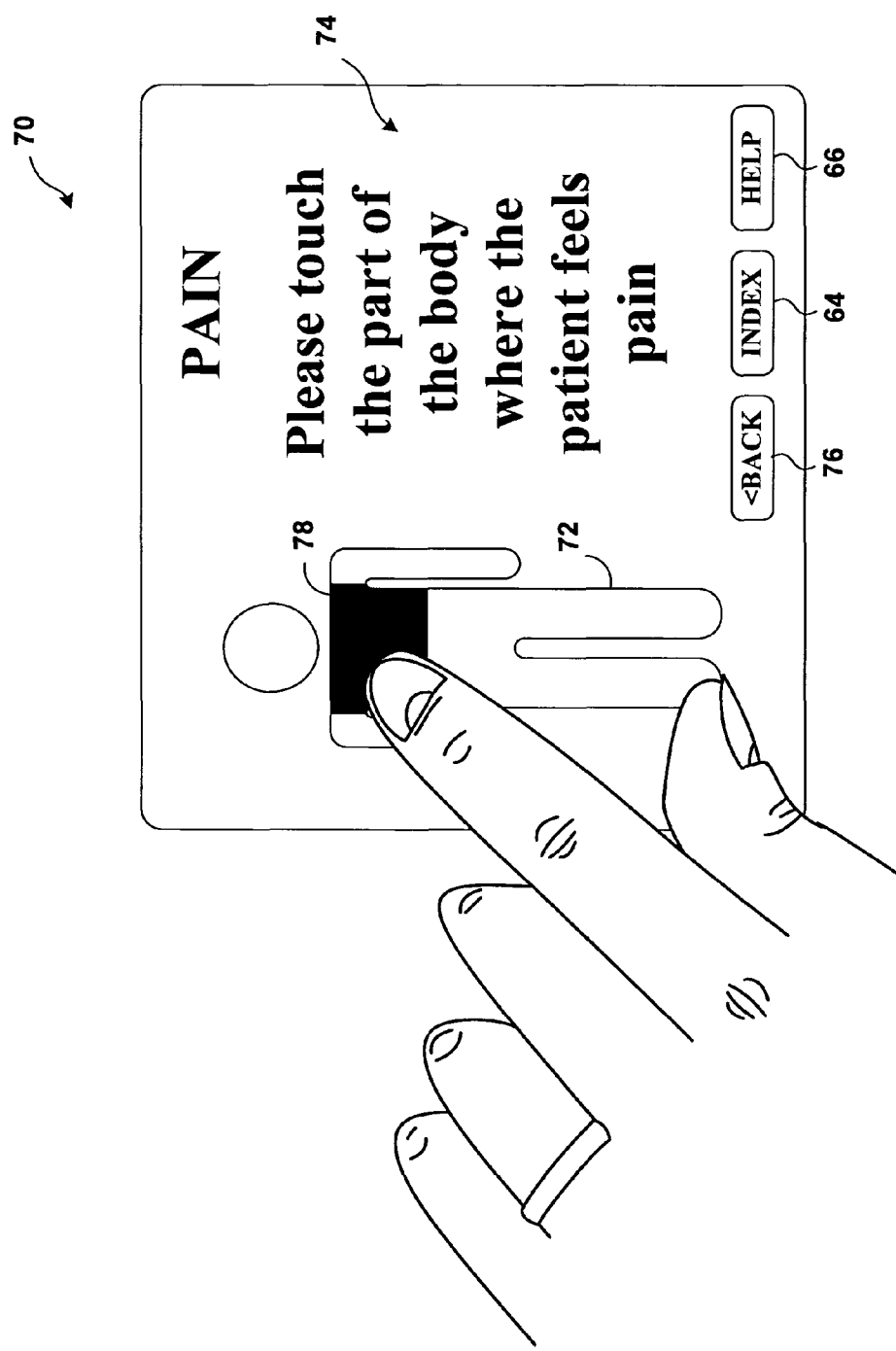
FIG. 4 is an exemplary screen display illustrating an interrogation with a diagram representing at least a portion of a human body, according to one embodiment of the invention.

FIG. 4 is an exemplary screen display 70 illustrating an interrogation technique. As shown in FIG. 4, the technique may be implemented in a first aid system having a touch screen, but may also be adapted for first aid systems having another pointing device, such as a pen or a mouse. The operator has previously entered patient status information to the effect that the patient is in severe pain, e.g., by touching the "Severe Pain" part of the screen shown in FIG. 3. In response to the patient status information, the first aid system interrogates further by presenting a diagram 72 representing a human body, along with an instruction 74 to the operator to touch the part of diagram 72 where the patient feels pain. In other words, the operator is directed to select a part of the displayed human body 72.

Had the operator incorrectly selected the "Severe Pain" option, the operator could undo the error by touching the "Back" option 76. Like the "Index" and "Help" options, the "Back" option may be available on several screen displays. Although not shown in the figures, a "Home" or "Start Over" option, or other navigational options, may also be presented.

In FIG. 4, the operator has selected the upper torso 76, which has been highlighted. When the first aid system receives the selection of a part of the displayed human body, the first aid system may present first aid information as a function of the selection, or may interrogate the operator further.

Figure 5:
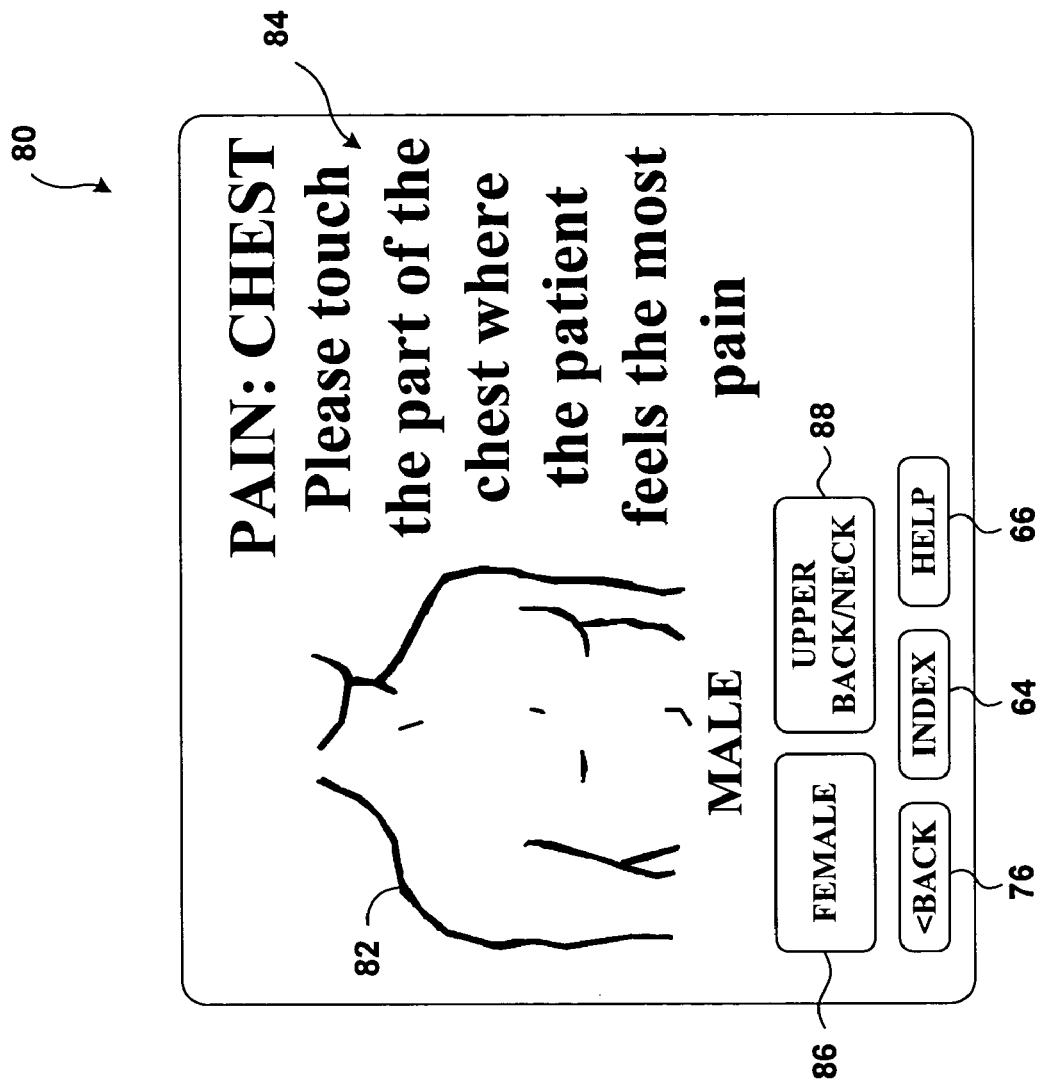
FIG. 5 is an exemplary screen display showing another interrogation with a more specific diagram representing a portion of a human body, according to another embodiment of the invention.

FIG. 5 is an exemplary screen display 80 showing a further interrogation. In response to the selection of the upper torso, the first aid system presents a diagram 82 of an upper chest, along with an instruction 84 to the operator to touch the part of the body where the patient feels pain. Diagram 82 shows a more specific region of the body than diagram 72 in FIG. 4. By interrogating about a more specific region of the body, the first aid system can narrow down the number of possible presumptive first aid diagnoses, and can focus on first aid for the particular problem experienced by the patient.

In cases in which the patient is already established as female, a diagram showing female anatomy may be displayed in place of a diagram showing male anatomy. In the event the gender of the patient has not yet been established, the operator may select a "Female" option 86, which may cause the first aid system to display of a female upper torso. In some circumstances, the anatomical differences between male and female may be important, and the operator may select the portion of the anatomy in which the patient feels pain. In variations of the invention, additional options may be presented, such as options to display diagrams for a child or an infant.

In cases in which the patient is experiencing upper back or neck pain, the operator may select an "Upper Back/Neck" option 88, which may cause the first aid system to display the upper back, rather than the chest.

Once again, the operator is directed to select a part of displayed human body 82. The first aid system receives the selection, and may display first aid information as a function of the selection, or may interrogate further.

Figure 6:
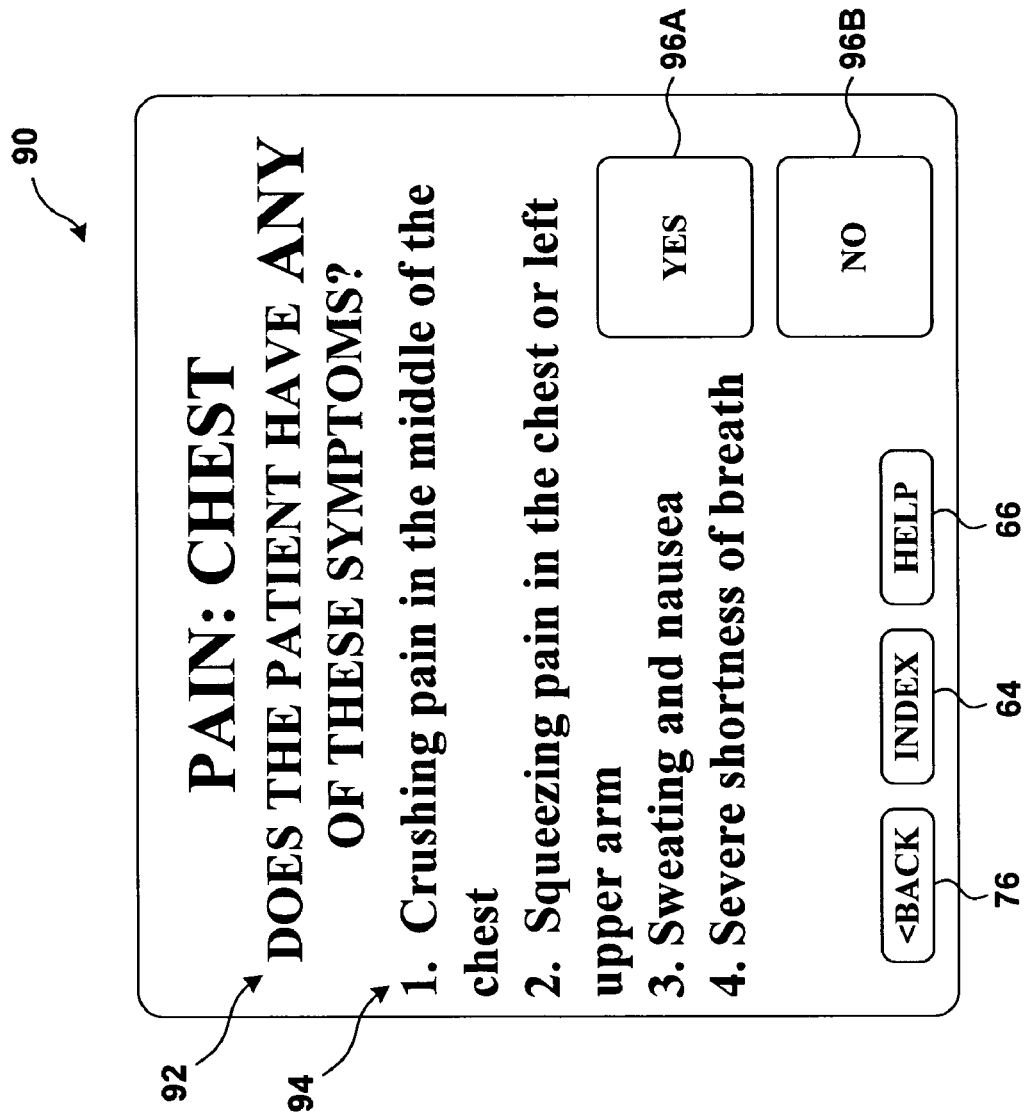
FIG. 6 is an exemplary screen display demonstrating another interrogation using a yes-no format, according to another embodiment of the invention.

FIG. 6 is an exemplary screen display 90 demonstrating a further interrogation without displaying a portion of a human body. In particular, screen display 90 is an example of what could be displayed should the patient select the center of the chest when touching human chest diagram 82 in FIG. 5. Pain in the center of the chest is often a symptom of a heart attack, and screen display 90 addresses this issue right away.

The first aid system presents an interrogation 92, asking the operator to report whether or not the patient is experiencing any of the symptoms in a list 94. The operator may answer the interrogation affirmatively by selecting the "Yes" option 96A, and may answer negatively by selecting the "No" option 96B.

Figure 7:
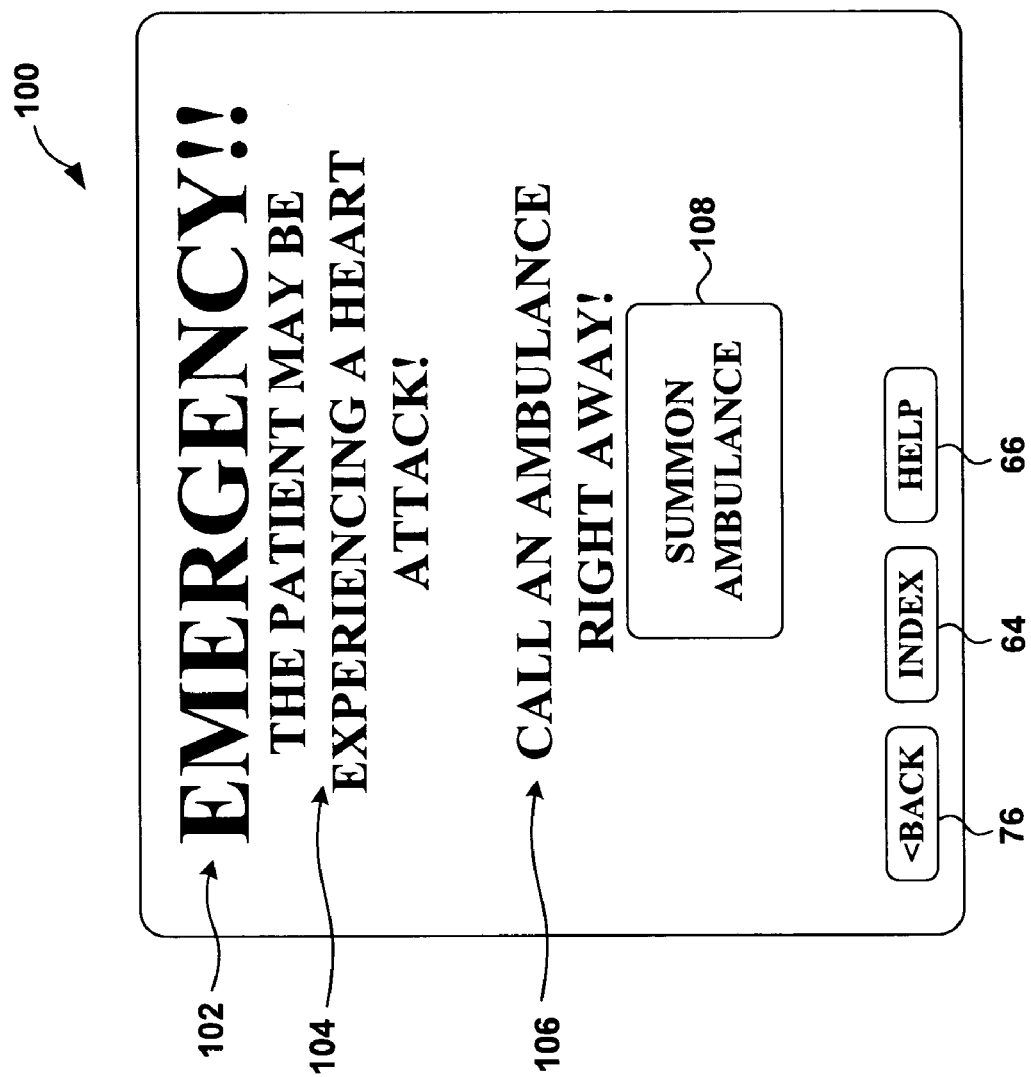
FIG. 7 is an exemplary screen display showing first aid information including a presumptive first aid diagnosis and a first aid instruction, according to an embodiment of the invention.

FIG. 7 is an exemplary screen display 100 that may be generated when the operator selects "Yes" in response to interrogation 92. Screen display 100 includes a written emergency alert 102, notifying the operator that the condition of the patient may be extremely serious, and that the patient should receive medical attention right away. Written emergency alert 102 may be accompanied by an audible alarm generated by an alarm module. Screen display 100 also includes a presumptive first aid diagnosis 104, specifically, that the patient may be experiencing a heart attack. Screen display 100 also includes a direction 106 that instructs the operator what to do, specifically, to summon an ambulance.

In addition, screen display 100 may include a "Summon Ambulance" option 108. The "Summon Ambulance" option allows the operator to summon emergency medical personnel without using the telephone. Selection of the "Summon Ambulance" option causes the microprocessor in the first aid system to send a message to emergency personnel via a communication module. In a typical application, the message may be sent to an emergency service, which in turn summons the ambulance.

In addition to or in place of an option to summon emergency medical personnel, screen display 100 may present information about obtaining medical help, such as the telephone number of a local rescue service. When the patient's identity has been previously established as described above, screen display 100 may also present information that may be useful to medical personnel, such as contact information for the personal physician of the patient, or the current patient prescriptions, the indicated hospital or insurance information.

Figure 8:
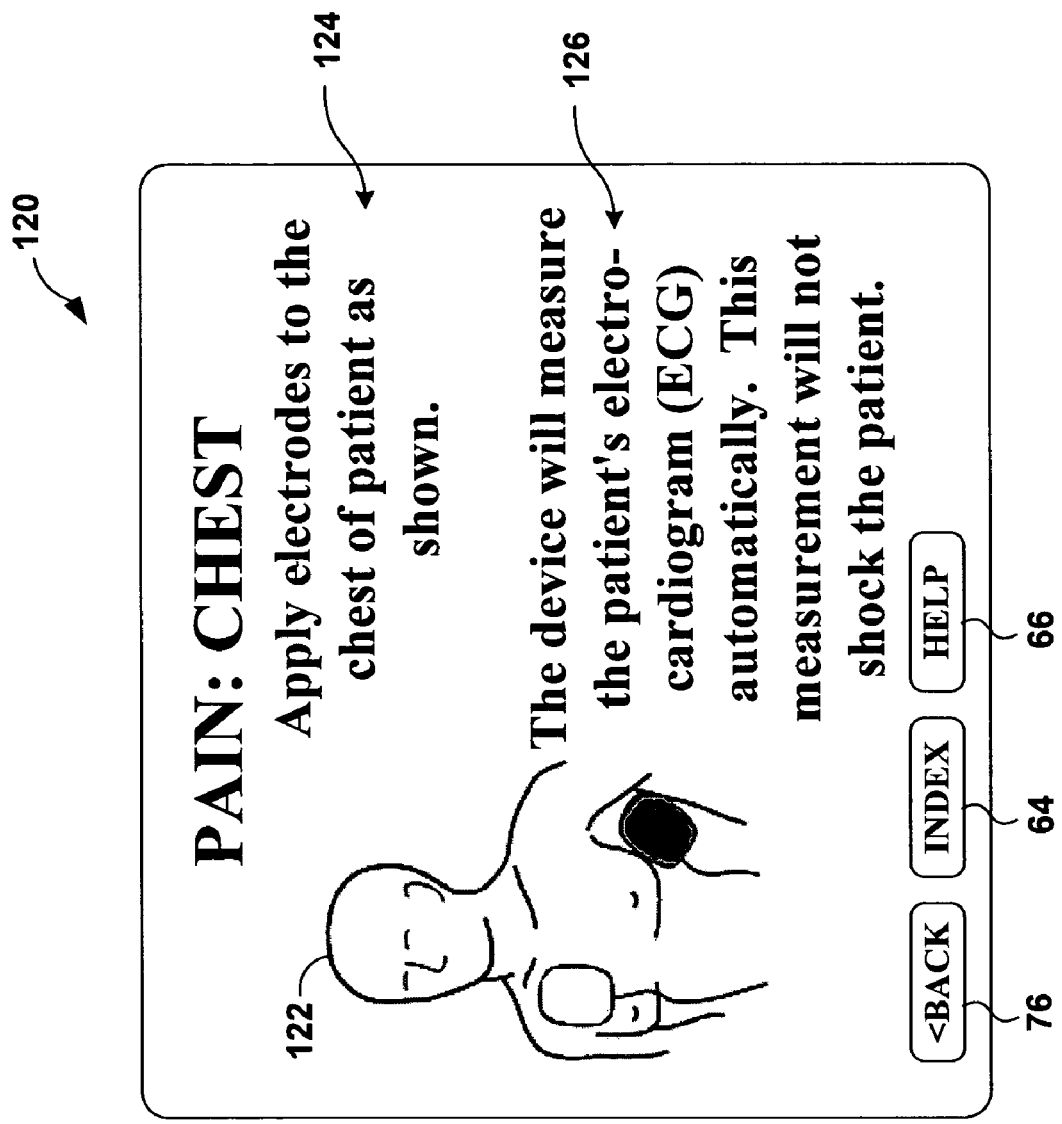
FIG. 8 is an exemplary screen display showing a direction to an operator that includes written and graphical instructions, according to an embodiment of the invention.

FIG. 8 is an exemplary screen display 120 that may be generated when the operator reports that the patient is experiencing chest pain. When the first aid system is incorporated with an external defibrillator, such as defibrillator 12 in FIG. 1, the first aid system may instruct the operator concerning deployment of electrodes 14, 16, to measure the ECG of the patient and evaluate the condition of the patient.

Screen display 120 includes a diagram 122 of a human figure with electrodes deployed on the chest in the correct manner. An instruction 124 directs the operator to apply the electrodes to the chest of the patient as shown in diagram 122. Screen display 120 further includes a brief explanation 126, explaining what the first aid system is about to do. The explanation may also assure the operator and the patient that measurement of the ECG does not involve a defibrillation shock.

Diagram 122 shows the operator how to position the electrodes on the patient. This deployment of electrodes facilitates reading of the ECG of the patient, and also facilitates delivery of a defibrillation shock should such a shock be needed.

In some cases, however, the ECG may be measured for reasons unrelated to administering a defibrillation shock. Indeed, the ECG may be measured when the patient is conscious exhibiting no need for defibrillation therapy. Accordingly, screen display 120, or a variation thereof, may be displayed when the operator has entered information indicating that the patient's condition is something other than chest pain. For example, the first aid system may present a variation of screen display 120 when the operator reports that the patient is unconscious, or when the operator reports that the patient is conscious but feels short of breath. An advantage of incorporating the first aid system with an external defibrillator is that the first aid system may use defibrillation electrodes or a set of dedicated ECG electrodes as sensors to acquire information about the condition of the patient without actually delivering defibrillation therapy. The first aid system may use the ECG to determine a presumptive diagnosis, or to refine a previous presumptive diagnosis.

Figure 9:
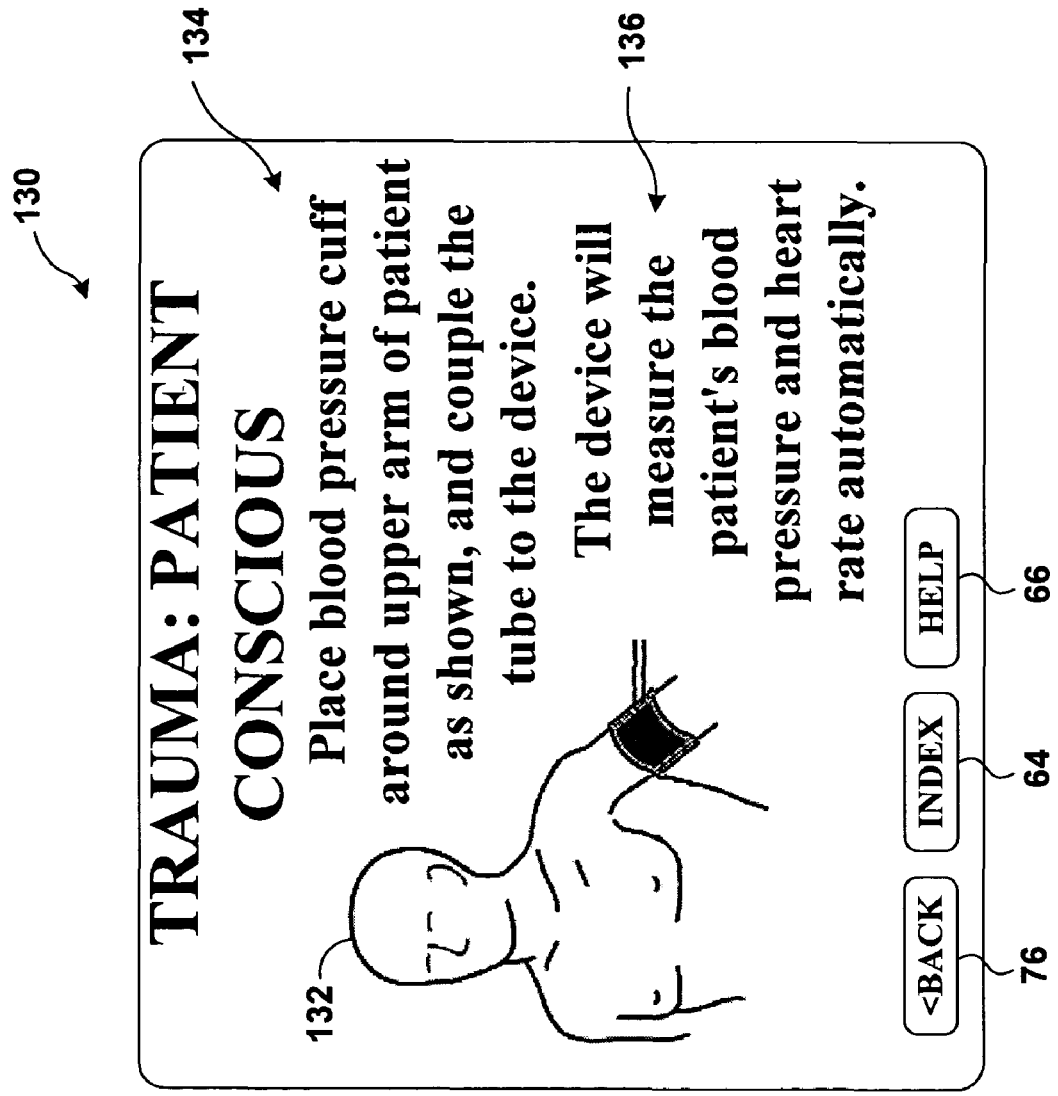
FIG. 9 is another exemplary screen display showing a direction to an operator that includes written and graphical instructions, according to an embodiment of the invention.

FIG. 9 is an exemplary screen display 130 illustrating a first aid instruction. In particular, FIG. 9 illustrates an instruction that directs the operator as to use of equipment. Screen display 130 includes a diagram 132 of a human figure with a blood pressure cuff deployed on the upper arm. An instruction 134 directs the operator to place the blood pressure cuff around the upper arm of the patient as shown in diagram 132. Screen display 130 further includes a brief explanation 136, explaining that the first aid system will measure the patient's blood pressure and heart rate. Blood pressure and heart rate are vital signs that may be important to medical personnel, and may further may be used by the first aid system to determine a presumptive first aid diagnosis.

Figure 10:
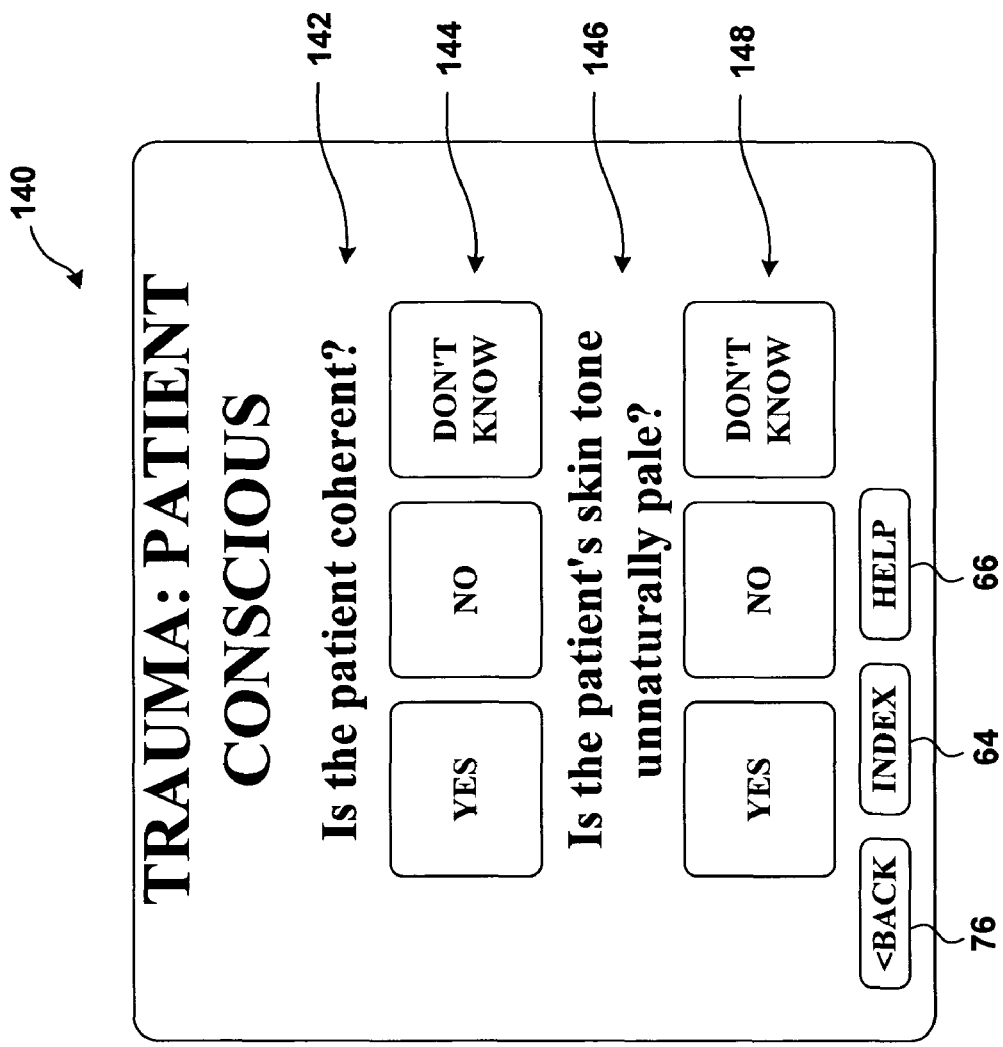
FIG. 10 is an exemplary screen display that includes multiple interrogations, according to an embodiment of the invention.

FIG. 10 is another exemplary screen display 140. The first aid system may generate screen display 140 in response to the measured heart rate and blood pressure. Should the patient have a low blood pressure, for example, the first aid system may interrogate the operator to determine whether the low blood pressure is having physical effects. A drop in blood pressure may indicate that the patient is going into shock.

Screen display 140 includes multiple interrogations. First interrogation 142 is accompanied by a first set of answer selections 144, and second interrogation 146 is accompanied by a second set of answer selections 148. Display of multiple interrogations may be appropriate when a potentially serious condition, such as shock, is possible. Display of multiple interrogations may also be appropriate the interrogations are not dependent upon on another. In FIG. 10, interrogations 142, 146 pertain to the coherence and skin tone of the patient. Some patient conditions may affect coherence, others may affect skin tone, and others, such as shock, may affect both.

Figure 11:
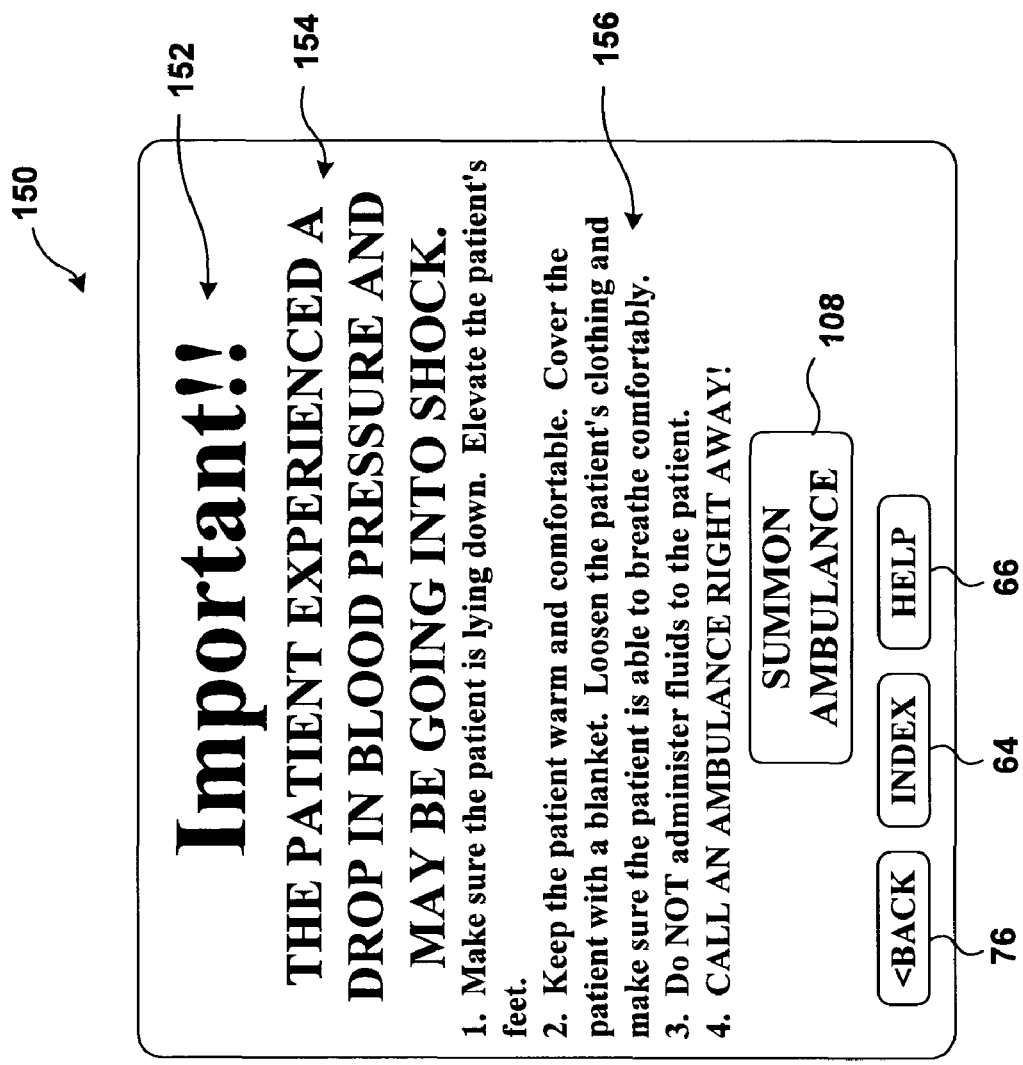
FIG. 11 is an exemplary screen display showing first aid information including a presumptive first aid diagnosis and a first aid instruction, according to an embodiment of the invention.

FIG. 11 is an exemplary screen display 150 showing first aid information. In particular, the first aid information includes a written alert 152, a presumptive first aid diagnosis 154, and directions to the operator to administer treatment 156. The first aid system has determined a presumptive diagnosis of shock, as a function of blood pressure measurements, the responses of the operator to interrogations, or both.

Written alert 152, which may be may be accompanied by an audible alarm generated by an alarm module, notifies the operator that the patient needs attention. Presumptive diagnosis 154 notifies the operator why the patient needs attention, and instructions 156 tell the operator what to do, and what not to do, to treat the patient for shock. Although the operator is instructed to summon an ambulance, the operator is further instructed how to treat the patient pending the arrival of emergency personnel.

As shown by FIGS. 3-11, interactions between the first aid system and the operator can lead to the determination of a presumptive first aid diagnosis and the presentation of first aid information. In general, through a series of interrogations, measurements and instructions, the first aid system collects patient status information. The first aid system focuses in on a presumptive first aid diagnosis that corresponds to the condition of the patient and informs the operator how to proceed.

Figure 12:
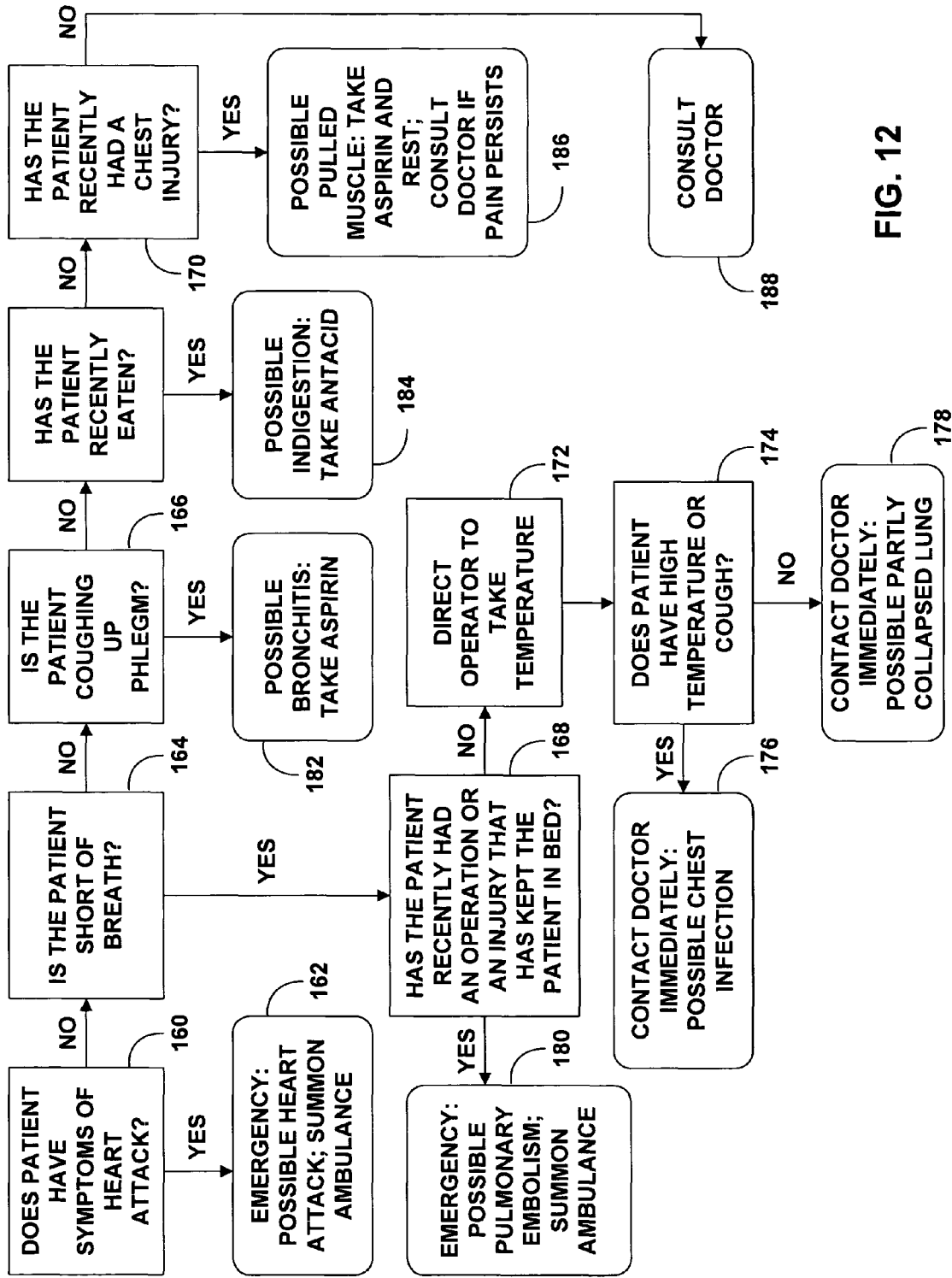
FIG. 12 is flow diagram illustrating an exemplary first aid procedure that can be applied by a first aid system.

FIG. 12 is flow diagram illustrating an exemplary technique by which a first aid system can determine a presumptive first aid diagnosis and present first aid information as a function of patient status information. In particular, the flow diagram of FIG. 12 illustrates a first aid procedure by which a first aid system can narrow down the number of possible presumptive first aid diagnoses, and can focus on first aid for the particular problem experienced by the patient.

In the example of FIG. 12, it is assumed that the patient has complained of chest pain. The first aid system interrogates the operator as to whether the patient has the symptoms of a heart attack (160), such as by presenting exemplary screen display 90 shown in FIG. 6 or by following a more detailed procedure shown in FIG. 13. If the operator responds in the affirmative, then the first aid system determines a presumptive diagnosis of heart attack (162) and may present information such as that shown in exemplary screen display 100 in FIG. 7.

When the response from the operator indicates that the patient does not have the symptoms of a heart attack, the first aid system continues to receive further patient status information. The first aid system may receive patient status information via interrogation of the operator. The interrogation may pertain to the current condition of the patient (e.g., 164, 166) or to the medical history of the patient (e.g., 168, 170). In some cases, the first aid system may have previously stored medical history for a particular patient. In those cases, questions pertaining to medical history may be omitted, or the operator may be asked to confirm the medical history.

In addition, the first aid system may receive patient status information via one or more sensors. The exemplary procedure includes at least one direction to the operator (172) to apply a sensor, such as a temperature sensor or blood pressure cuff, to the patient. The first aid system may use patient status information obtained via the sensor (174) to determine a presumptive diagnosis (176, 178).

In the exemplary procedure shown in FIG. 12, the first aid system recommends a course of action for the operator or patient or both. In some cases, the presumptive diagnosis indicates that the condition of the patient is serious, and so the first aid system recommends that the patient obtain prompt, professional medical care (162, 176, 178, 180). In other cases, the first aid system does not recommend the patient needs professional medical care. In those cases, the operator or the patient may be instructed about appropriate home therapy or medication (182, 184, 186). In the event that the patient status information does not result in a presumptive diagnosis, the first aid system may include an instruction that the patient should consult a physician (188).

The first aid system may apply various procedures for a variety of conditions. The procedures, which may be represented as flow diagrams like FIG. 12, may be directed to a variety of illnesses, injuries, and other health-related concerns. The invention encompasses procedure and flow diagrams for a variety of health-related concerns, and is not limited to chest pain. In addition, the invention is not limited to the procedure for addressing chest pain shown in FIG. 12. The procedure may change depending upon what sensors are available. For example, a first aid system incorporated with a defibrillator may apply a procedure that directs the operator to apply electrodes to the chest of the patient, such as exemplary screen display 120 shown in FIG. 8.

From time to time, a particular procedure for addressing a particular health-related concern may be updated or improved. The procedure may take into account new diseases, new medications, new methods of treatment, new diagnostic techniques, and the like. Also, new procedures may be added, or the procedures may be customized for a particular patient, venue, geographical region, or the like.

Figure 13:
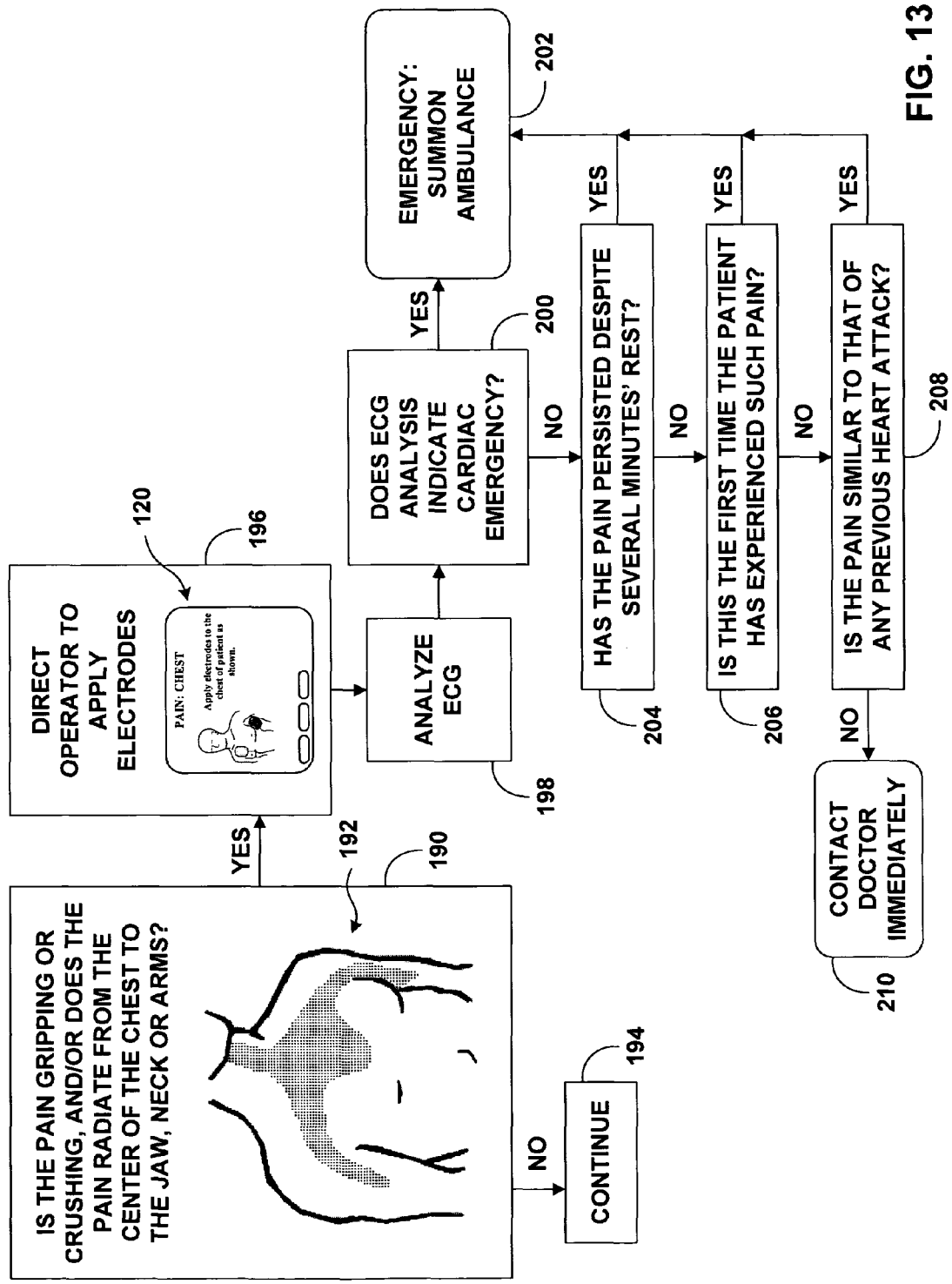
FIG. 13 is a flow diagram illustrating an exemplary first aid sub-procedure that can be included in the procedure shown in FIG. 12.

FIG. 13 is flow diagram illustrating a first aid procedure that may be a sub-procedure of the first aid procedure shown in FIG. 12. In the example of FIG. 13, it is again assumed that the patient has complained of chest pain. Instead of presenting exemplary screen display 90 shown in FIG. 6, the first aid system may interrogate apply a modified procedure. In particular, the first aid system may ask whether the patient is experiencing physical symptoms of a heart attack (190), i.e., whether the patient is experiencing pain in certain parts of the body. The interrogation may include a diagram 192 showing the parts of the body that may be affected if the patient is suffering a heart attack.

If the patient does not have pain consistent with a heart attack, the first aid system may continue the interrogation (194), e.g., by asking whether the patient is short of breath (164 in FIG. 12). If, on the other hand, the patient does complain of pain consistent with a heart attack, the first aid system may direct the operator to apply sensors to evaluate the heart rhythm of the patient. When the first aid system is incorporated with a defibrillator, for example, the operator may be directed to apply defibrillation electrodes 14 and 16. An instruction such as exemplary screen 120 shown in FIG. 8 may be presented to tell the operator how to apply the electrodes.

When the sensors are coupled to the patient, the first aid system analyzes the ECG of the patient (198). When analysis of the ECG indicates a cardiac emergency (200), the first aid system summons medical help at once or directs the operator to do so (202). The first aid system may also interrogate the operator further about the current condition of the patient or the medical history of the patient (204, 206, 208) and may determine a presumptive diagnosis of heart attack as a function of the received patient status information. In alternate embodiments, interrogations about current condition and medical history (204, 206, 208) may be performed before or during ECG analysis (198).

In the event that the first aid system is unable to reach a presumptive diagnosis of heart attack, the first aid system may nevertheless direct the patient to seek medical help immediately (210).

Figure 14:
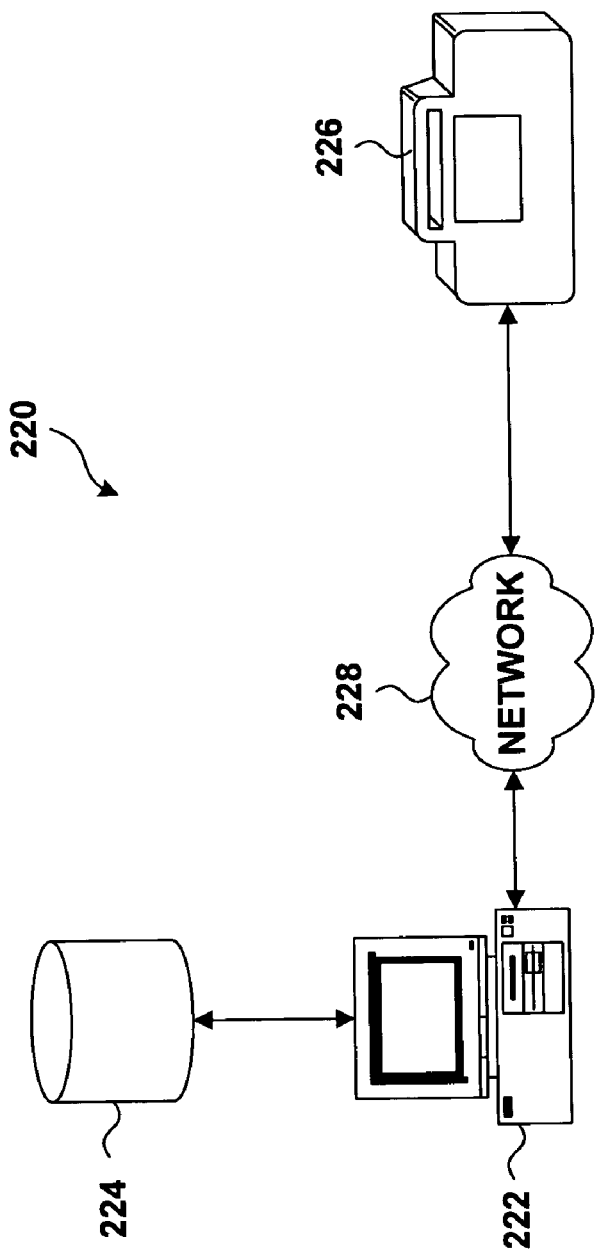
FIG. 14 is a schematic diagram of an exemplary system for updating first aid procedures applied by a first aid system.

FIG. 14 is a schematic diagram of an exemplary system 220 for updating first aid procedures. A central server 222 stores a plurality of first aid procedures in a storage element 224. Storage 224 may be any medium for storing computer-readable instructions or data, such as a magnetic or optical storage medium.

Server 222 communicates with a client first aid system 226 via a communications network 228. Network 228 may be any network, including a local network, the Internet, a telephone network or a wireless communication network. First aid system 226 may connect to network 228 via a communication module. The communication may be initiated by server 222 or client first aid system 226.

Server 222 may interrogate client first aid system 226 as to the set of first aid procedures being implemented by client first aid system 226. When an update is appropriate, server 222 may download new or updated procedures to client first aid system 226 via network 228. Client first aid system 226 receives and stores the procedures.

Figure 15:
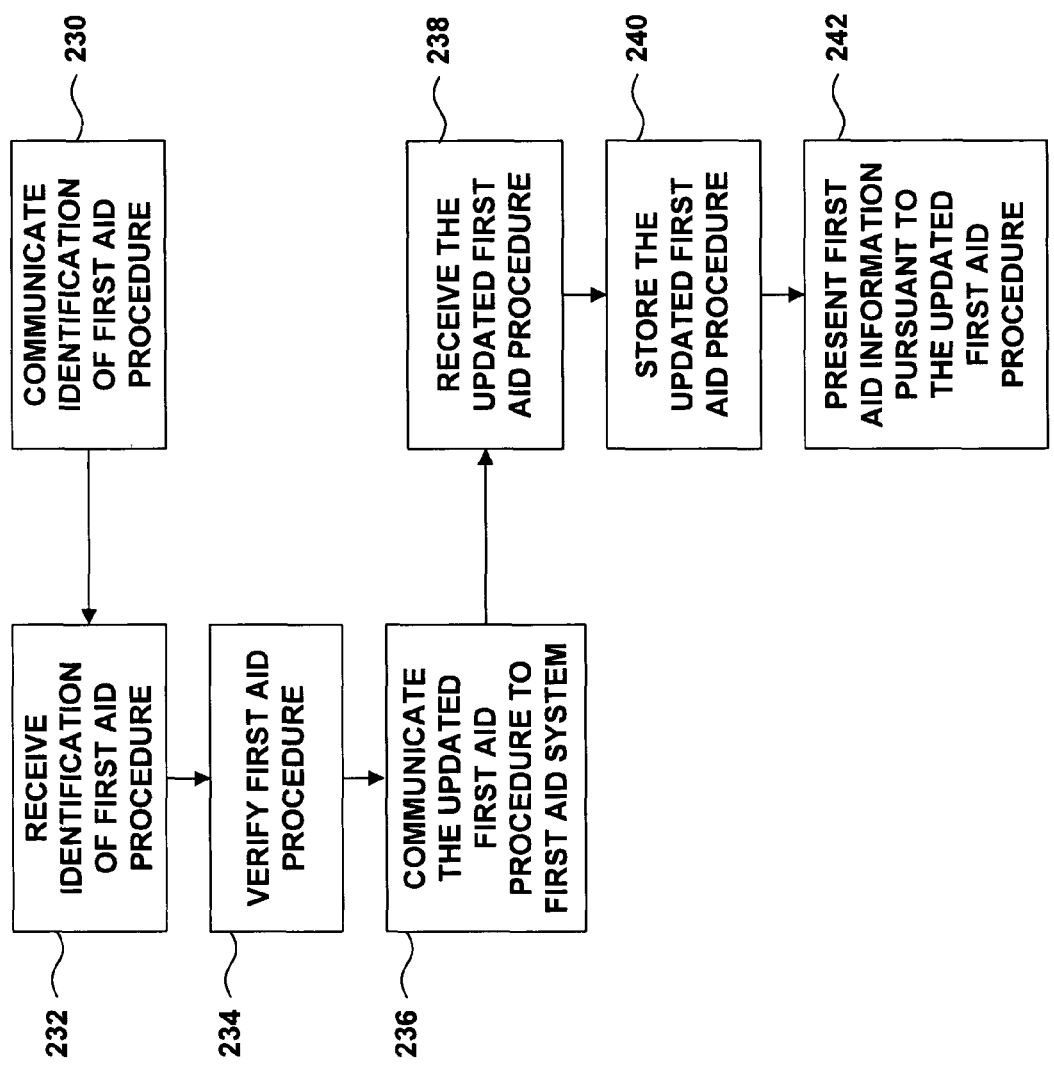
FIG. 15 is a flow diagram illustrating an exemplary technique for updating first aid procedures applied by a first aid system.

FIG. 15 is a flow diagram illustrating an exemplary technique for updating first aid procedures. Client first aid system 226 communicates an identification of one or more first aid procedures to server 222 (230), and may do so in response to an interrogation from server 222. First aid procedures may be identified by a code number, version number, or any other identifier. Upon receiving the identification (232), server 222 verifies the first aid procedure (234) and determines whether an update is indicated. When an update is indicated, server 222 retrieves an updated procedure from storage site 224 and communicates the updated first aid procedure to client first aid system 226 (236).

Client first aid system 226 receives the update (238) and stores it in memory (240). Storing the updated first aid procedure may include deleting an older procedure and replacing the older procedure with the updated procedure. Storing the updated procedure may also include retaining the older procedure but incorporating updates to the older procedure. Storing the updated procedure may further include adding a sub-procedure to an older procedure. When used by an operator attending to a patient, client first aid system 226 may apply the updated first aid procedure (242).

Figure 16:
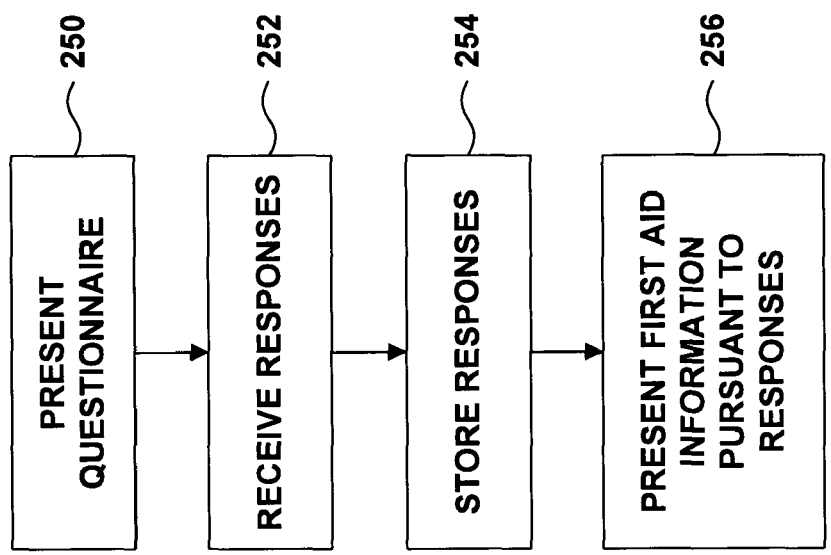
FIG. 16 is a flow diagram illustrating a technique for collecting patient status information about one or more particular patients.

FIG. 16 is a flow diagram illustrating an exemplary technique for collecting patient status information about one or more particular patients. As discussed above, an embodiment of the invention can be principally for the benefit of specific individuals, such as the members of a family residing in a household. Patient status information pertaining to the anticipated patients may be entered into the first aid system before a need for first aid arises.

The first aid system may collect patient status information in any of several ways. One way is to present a questionnaire (250), asking for information about the potential patient. The questionnaire may ask for the name of the patient, age or birth date, gender, ethnicity, blood type, height, weight, and the like. The questionnaire may ask questions about current practices, such as questions about alcohol or tobacco usage. The questionnaire may also collect information about medical history, such as surgery, implants, trauma, heart attacks, high blood pressure, allergies, respiratory problems and so forth. The questionnaire may inquire into medications taken by the patient. The questionnaire may further ask for information about a doctor or doctors for the patient, along with contact information. The questionnaire may ask for information about insurance coverage. The first aid system may ask for other kinds of information as well.

The first aid system receives the responses (252) and stores the responses in memory (254). The responses are associated with the identity of the particular patient. Some patient status information, such as the age of the patient, may be updated automatically by the first aid system. Other patient status information, such as height, weight and tobacco usage habits, which may or may not vary substantially over time, may be updated if the patient status information changes. Further, some patient status information may be updated automatically following use of the first aid system. If the patient exhibits high blood pressure, for example, the first aid system may update the medical history of the patient to reflect the high blood pressure.

In a first aid situation, the first aid system presents first aid information according to the stored patient status information (256). In an embodiment mentioned above, an introductory screen can present a list of possible patients, and selection of a patient from the list causes the previously stored patient status information to be retrieved. The patient can also be identified with a sensor such as a fingerprint sensor.

When the patient has been identified, the first aid system retrieves from memory the patient status information associated with the identified patient, and presents first aid information as a function of the retrieved patient status information. The first aid system can, for example, present a human body diagram appropriate for the age and gender of the patient. The first aid system may also use medical history rather than interrogating an operator, or may ask the operator to confirm the medical history. The medical history can assist first aid system in making some decisions more quickly. The first aid system can also reach a presumptive diagnosis as a function of previously entered patient status information.

The invention may offer several advantages. By employing the invention, the operator not trained to provide medical care can respond to a medical condition quickly. Based upon information received via electrodes, input devices and sensors, the first aid system can determine a presumptive diagnosis and show the operator how to proceed. The invention helps guide the untrained operator until trained medical personnel arrive or the emergency is resolved.

The interactions between the first aid system and the operator can be arranged logically and intuitively, so that the operator will be able to use the first aid system effectively. Various embodiments of the invention may incorporate warning signals, large writing, simple diagrams, and plain language to assist the operator and avoid confusion.

The invention is versatile. The invention may be embodied with a variety of medical devices, or may be embodied as a "stand-alone" device. The invention may be embodied with a variety of input and output devices, and with an assortment of sensors. The displayed text and graphic information may be adapted to particular geographic locations. Furthermore, invention encompasses updates so that a first aid system may apply new, improved or customized first aid procedures.

The invention accommodates updates and customization. A first aid system may download new or updated first aid procedures from a remote source. As a result, the first aid system can stay current on various health-related matters and first aid procedures. A first aid system may also be customized to particular patients, making presentation of first aid information more efficient for those patients.

When the invention is incorporated with an external defibrillator, the external defibrillator takes on additional functionality. In particular, use of the defibrillator need not be limited to serious emergencies. Instead, the defibrillator may be used for less urgent first aid situations. The availability of AEDs at various venues may make the added functionality attractive. In the case of a medical emergency, an operator need not worry whether to retrieve a first aid kit or an AED, but may readily retrieve both at the same time.

Various embodiments of the invention have been described. These specific embodiments are illustrative of the practice of the invention. Various modifications may be made without departing from the scope of the claims. For example, the screen displays depicted in the figures are for illustrative purposes. A first aid system may present information in many other ways.

The invention need not be incorporated in a single device. A first aid system may comprise a plurality of devices. A first aid system may include discrete sensors or therapy devices, for example, which communicate with one another via wireless or hardwired connections.

The invention need not address a full range of first aid concerns. In some embodiments of the invention, the first aid system may be configured to address a restricted number of first aid concerns. In some embodiments of the invention, the first aid system may obtain patient status information for a presumptive first aid diagnosis from sensors, without operator interrogation.

The patient status information may be stored in memory for later retrieval. In an emergency, for example, emergency personnel or hospital personnel may retrieve patient status information from the first aid system. The retrieved patient status information may be useful in diagnosing or treating the patient, and result in a more complete medical record for the patient. It may also be useful to retrieve first aid information stored in memory. An output device included in the first aid system, such as a serial port or a printer, can output the patient status information and the first aid information stored in the memory. In another variation, the memory module may in a removable form, such as a memory stick, magnetic card or a floppy disk, and patient status information may be retrieved by retrieving the memory module from the first aid system.

The invention includes software to carry out the techniques described herein. The invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled through a network.

The invention may also be embodied as one or more devices that include logic circuitry to carry out the functions or methods as described above. The logic circuitry may include a processor that may be programmable for a general purpose or may be dedicated, such as microcontroller, a microprocessor, a Digital Signal Processor (DSP), Application Specific Integrated Circuit (ASIC), and the like. These and other embodiments are within the scope of the following claims.

The invention claimed is:

1. A method comprising:
    displaying, by a device, a diagram representing at least a portion of a human body;
    receiving, by the device, a selection made by a user of the device of a part of the diagram representing the at least a portion of the human body;
    presenting, by the device, first aid information as a function of the selection; and
    performing, by the device, at least one step selected from the group consisting of: summoning emergency medical personnel as a function of the selection, delivering an electrotherapy to a patient, and generating an audible alarm as a function of the selection.

2. The method of claim 1, in which the electrotherapy comprises a defibrillation therapy.

3. The method of claim 1, wherein performing, by the device, at least one step comprises performing, by the device, at least one step selected from the group consisting of: summoning emergency medical personnel as a function of the selection, and delivering an electrotherapy to a patient.

4. A computer-readable medium comprising instructions for causing a programmable processor to:
    display a diagram representing at least a portion of a human body;
    receive a selection made by a user of a part of the diagram representing the at least a portion of the human body; and
    present first aid information as a function of the selection,
    the instructions further causing the programmable processor to execute at least one step selected from the group consisting of: summon emergency medical personnel as a function of the selection, deliver a therapy to a patient as a function of the selection, and generate an audible alarm as a function of the selection.

5. The computer-readable medium of claim 4, wherein the instructions that cause the programmable processor to execute at least one step comprise instructions that cause the programmable processor to execute at least one step selected from the group consisting of: summon emergency medical personnel as a function of the selection, and deliver a therapy to a patient as a function of the selection.

* * * * *

UNITED STATES PATENT AND TRADEMARK OFFICE
CERTIFICATE OF CORRECTION

| | | |
|---|---|---|
| PATENT NO. | : 7,623,915 B2 | Page 1 of 1 |
| APPLICATION NO. | : 10/620742 | |
| DATED | : November 24, 2009 | |
| INVENTOR(S) | : Sullivan et al. | |

It is certified that error appears in the above-identified patent and that said Letters Patent is hereby corrected as shown below:

Column 17, line 12, (too many spaces) "Various  embodiments  of  the  invention  have  been  described"

Should read -- Various embodiments of the invention have been described --

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

PATENT NO.       : 7,623,915 B2                                   Page 1 of 1
APPLICATION NO.  : 10/620742
DATED            : November 24, 2009
INVENTOR(S)      : Sullivan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1625 days.

Signed and Sealed this

Twenty-sixth Day of October, 2010

David J. Kappos
*Director of the United States Patent and Trademark Office*